United States Patent
Ford et al.

(10) Patent No.: US 11,946,939 B2
(45) Date of Patent: *Apr. 2, 2024

(54) BIOMARKERS AND METHODS FOR ASSESSING MYOCARDIAL INFARCTION AND SERIOUS INFECTION RISK IN RHEUMATOID ARTHRITIS PATIENTS

(71) Applicants: LABORATORY CORPORATION OF AMERICA HOLDINGS, Burlington, NC (US); UAB RESEARCH FOUNDATION, Birmingham, AL (US)

(72) Inventors: Kerri Ford, South San Francisco, CA (US); Jeffrey R. Curtis, Birmingham, AL (US)

(73) Assignee: Laboratory Corporation of America Holdings, Burlington, NC (US)

( * ) Notice: Subject to any disclaimer, the term of this patent is extended or adjusted under 35 U.S.C. 154(b) by 83 days.

This patent is subject to a terminal disclaimer.

(21) Appl. No.: 17/201,985

(22) Filed: Mar. 15, 2021

(65) Prior Publication Data

US 2021/0199671 A1 Jul. 1, 2021

Related U.S. Application Data

(63) Continuation of application No. 16/814,530, filed on Mar. 10, 2020, now Pat. No. 10,962,552, which is a continuation of application No. PCT/US2018/050817, filed on Sep. 13, 2018.

(60) Provisional application No. 62/558,436, filed on Sep. 14, 2017.

(51) Int. Cl.
    *G01N 33/68* (2006.01)
    *G16H 10/40* (2018.01)
    *G16H 50/20* (2018.01)

(52) U.S. Cl.
    CPC ......... *G01N 33/6893* (2013.01); *G16H 10/40* (2018.01); *G16H 50/20* (2018.01); *G01N 2333/4737* (2013.01); *G01N 2333/575* (2013.01); *G01N 2800/52* (2013.01); *G01N 2800/54* (2013.01); *G01N 2800/60* (2013.01)

(58) Field of Classification Search
    CPC ....... G01N 33/6893; G01N 2333/4737; G01N 2800/52; G01N 2800/54; G01N 2800/60; G16H 10/40; G16H 50/20
    See application file for complete search history.

(56) References Cited

U.S. PATENT DOCUMENTS

| | | | |
|---|---|---|---|
| 4,230,797 A | 10/1980 | Boguslaski et al. | |
| 4,233,402 A | 11/1980 | Maggio et al. | |
| 4,275,149 A | 6/1981 | Litman et al. | |
| 4,376,110 A | 3/1983 | David et al. | |
| 4,659,678 A | 4/1987 | Forrest et al. | |
| 4,727,022 A | 2/1988 | Skold et al. | |
| 5,744,305 A | 4/1998 | Fodor et al. | |
| 9,200,324 B2 | 12/2015 | Cavet et al. | |
| 10,962,552 B2 | 3/2021 | Ford et al. | |
| 2014/0303902 A1 | 10/2014 | Alaupovic | |
| 2015/0064132 A1 | 3/2015 | Graham | |
| 2017/0168070 A1 | 6/2017 | Oberoi | |
| 2019/0311789 A1* | 10/2019 | Barr | G16B 20/00 |
| 2020/0371113 A1* | 11/2020 | Brenner | G01N 33/6893 |

FOREIGN PATENT DOCUMENTS

| | | | |
|---|---|---|---|
| JP | 2013508719 A | 3/2013 | |
| WO | 9735037 A1 | 9/1997 | |
| WO | 2004056456 A1 | 7/2004 | |
| WO | 2004088309 A1 | 10/2004 | |
| WO | 2015191423 A1 | 12/2015 | |
| WO | WO-2017136464 A1 * | 8/2017 | A61B 5/02 |

OTHER PUBLICATIONS

Graf (PLOS One 2009 4:e6242) (Year: 2009).*
Westlake (Rheumatology 2010 49:295-307). (Year: 2010).*
Kofoed (Critical Care 2007 11:R38), (Year: 2007).*
Oncul (Diabetes Care 2002 25:p. 937), (Year: 2002).*
Au (Ann Rheum Dis 2011 70:785) (Year: 2011).*
Gremese et al. "The Metabolic Syndrome: The Crossroads between Rheumatoid Arthritis and Cardiovascular Risk" Autoimmunity Reviews 2011 10:582-589 (Year: 2011).*
Banerjee et al. "Cardiovascular Outcomes in Male Veterans with Rheumatoid Arthritis" Am J. Cardiol. 2008 101:1201-1205 (Year: 2008).*
Turkyilmaz et al. "Relationship between Pulse Wave Velocity and Serum YKL-40 Level in Patients with Early Rheumatoid Arthritis" Rheumatol. 2013 33:2751-2756 (Year: 2013).*
Bonek et al., "Cardiovascular risk assessment in rheumatoid arthritis-controversies and the new approach", Reumatologia., 2016;54(3):128-35. doi: 10.5114/reum.2016.61214. Epub Jul. 18, 2016.
Curtis, et al., "Biomarker-related risk for myocardial infarction and serious infections in patients with rheumatoid arthritis: a population-based study", Ann Rheum Dis., Mar. 2018;77(3):386-392. doi: 10.1136/annrheumdis-2017-211727. Epub Dec. 21, 2017. (Abstract Only).
International Search Report issued in PCT/US2018/050817 dated Jan. 23, 2019 (5 pages).
Lopez-Mejias Raquel et al: "Cardiovascular risk assessment in patients with rheumatoid arthritis: The relevance of clinical, genetic and serological markers", Autoimmunity Reviews, Elsevier, Amsterdam, NL, vol. 15, No. 11, Aug. 1, 2016 (Aug. 1, 2016), pp. 1013-1030, XP029773799, ISSN: 1568-9972, DOI: 10.1016/J.AUTREV.2016.07.026.

(Continued)

*Primary Examiner* — Changhwa J Cheu
(74) *Attorney, Agent, or Firm* — Kilpatrick Townsend & Stockton LLP

(57) ABSTRACT

Provided herein are methods for assessing risk of infection or cardiovascular disease (CVD) in a subject with an inflammatory disease, e.g., rheumatoid arthritis. The methods include performing immunoassays to generate scores based on quantitative data for expression of biomarkers relating to inflammatory biomarkers with or without additional clinical variables to assess infection and CVD risk. Also provided are uses of inflammatory biomarkers for guiding treatment decisions.

18 Claims, 3 Drawing Sheets

(56) References Cited

OTHER PUBLICATIONS

Mehmet Kadri Akboga et al: "Effect of serum YKL-40 on coronary collateral development and Syntax score in stable coronary artery disease", International Journal of Cardiology, Elsevier, Amsterdam, NL, vol. 224, Sep. 17, 2016 (Sep. 17, 2016), pp. 323-327, XP029774537, ISSN: 0167-5273, DOI: 10.1016/J.IJCARD.2016.09.042.
Wagan, et al., "Cardiovascular risk score in Rheumatoid Arthritis", Pak J Med Sci., May-Jun. 2016;32(3):534-8. doi: 10.12669/pjms.323.9779.
Written Opinion issued in PCT/US2018/050817 dated Jan. 23, 2019 (8 pages).
Zegkos, et al., "Cardiovascular risk in rheumatoid arthritis: assessment, management and next steps", TTher Adv Musculoskelet Dis., Jun. 2016;8(3):86-101. doi: 10.1177/1759720X16643340. Epub Apr. 30, 2016.
Akboga, et al., "Effect of Serum YKL-40 on Coronary Collateral Development and Syntax Score in Stable Coronary Artery Disease", International Journal of Cardiology, vol. 224, 2016, pp. 323-327.
Breiman et al., "Predicting Multivariate Responses in Multiple Linear Regression," J. R. Statist. Soc. B, vol. 59(1), 1997: pp. 3-54 (Document split into two parts because USPTO—formatted file is larger than Patent Center or EFS—Web allows for one file).
Chambless et al., "Association of Coronary Heart Disease Incidence with Carotid Arterial Wall Thickness and Major Risk Factors: The Atherosclerosis Risk in Communities (ARIC) Study, 1987-1993," Am J Epidemiol, vol. 146(6), 1997: pp. 483-494.
Curtis et al., "Validation of a Novel Multibiomarker Test to Assess Rheumatoid Arthritis Disease Activity," Arthritis Care & Research, vol. 64(12), Dec. 2012: pp. 1794-1803.
EP18855308.5, "Extended European Search Report", dated Jun. 24, 2021, 13 pages.
EP18855308.5, "Intention to Grant", dated Mar. 27, 2023, 9 pages.
EP18855308.5, "Office Action", dated Feb. 15, 2022, 6 pages.
Hodis et al, "The Role of Carotid Intima-Media Thickness in Predicting Clinical Coronary Events," Annals of Internal Medicine, vol. 128(4), Feb. 15, 1998: pp. 262-269.
JP2020-515675, "Office Action", dated Apr. 4, 2023, 5 pages.
JP2020-515675, "Office Action", dated Sep. 6, 2022, 10 pages.
Kisner, "Talking about Technology Product Development: The Making of the Abbott Architecttm" Clin. Lab. Manage. Rev., vol. 11(6), Nov.-Dec. 1997: pp. 419-421.
Lin et al., "Checking the Cox Model with cumulative sums of martingale-based residuals," Biometrika, vol. 80(3), Sep. 1993: pp. 557-572.
Mallya et al., "Correlation of Clinical Parameters of Disease Activity in Rheumatoid Arthritis with Serum Concentration of C-Reactive Protein and Erythrocyte Sedimentation Rate," The Journal of Rheumatology, vol. 9(2), 1982: pp. 224-228.
Ognibene et al., "A New Modular Chemiluminescence Immunoassay Analyser Evaluated," Clin Chem Lab Med, vol. 38(3), 2000: pp. 251-260.
Park et al., "Three-Year Experience in Using Total Laboratory Automation System," Southeast Asian J. Trop Med Public Health, vol. 33(Suppl. 2), 2002: pp. 68-73.
Pauli et al., "The Abbott Architect c8000: Analytical Performance and Productivity Characteristics of a New Analyzer Applied to General Chemistry Testing," Clin. Lab., vol. 51(1-2), 2005: pp. 31-41.
Salonen et al., "Ultrasonographically Assessed Carotid Morphology and the Risk of Coronary Heart Disease," Arteriosclerosis and Thrombosis, vol. 11(5), Sep./Oct. 1991: pp. 1245-1249.
Solomon, et al., "Disease Activity in Rheumatoid Arthritis and the Risk of Cardiovascular Events", Arthritis & Rheumatology, vol. 67, No. 6, Mar. 16, 2015, pp. 1449-1455.
Van Der Heijde et al., "Judging disease activity in clinical practice in rheumatoid arthritis: first step in the development of a disease activity score," Annals of the Rheumatic Diseases, vol. 49(11), 1990: pp. 916-920.
Van Leeuwen et al., "The Acute-Phase Response in Relation To Radiographic Progression in Early Rheumatoid Arthritis: a Prospective Study During the First Three Years of the Disease," Br. J. Rheum., vol. 32(suppl.), Jun. 1993: pp. 9-13.
Vasan, "Biomarkers of Cardiovascular Disease Molecular Basis and Practical Considerations," Circulation, vol. 113 (19), May 16, 2006: pp. 2335-2362 (Document split into two parts because USPTO—formatted file is larger than Patent Center or EFS—Web allows for one file).
Vicenzini et al., "Common Carotid Artery Intima-Media Thickness Determinants in a Population Study," J. Ultrasound Med, vol. 26, 2007: pp. 427-432.
Wilson et al., "Architect c16000 Clinical Chemistry Analyzer Sub-System Level Performance," American Association for Clinical Chemistry Annual Meeting, Clinical Chemistry, vol. 52(6), Supplement, 2006: pp. A199-A200.
Wirth et al., "Post-translational modification detection using metastable ions in reflector matrix-assisted laser desorption/ionization-time of flight mass spectrometry," Proteomics, vol. 2(10), Nov. 4, 2002: pp. 1445-1451.
Wolfe, "Comparative Usefulness of C-Reactive Protein and Erythrocyte Sedimentation Rate in Patients with Rheumatoid Arthritis," The Journal of Rheumatology, vol. 24(8), Aug. 1997, pp. 1477-1485.

\* cited by examiner

BIOMARKERS AND METHODS FOR ASSESSING MYOCARDIAL INFARCTION AND SERIOUS INFECTION RISK IN RHEUMATOID ARTHRITIS PATIENTS

This application is a continuation of U.S. patent application Ser. No. 16/814,530 filed Mar. 10, 2020, now U.S. Pat. No. 10,962,552, which is a continuation of International Patent Application No. PCT/US2018/050817, filed Sep. 13, 2018, which claims priority benefit to U.S. Application No. 62/558,436, filed Sep. 14, 2017, the entire contents of each of which are hereby incorporated by reference.

BACKGROUND

This application is directed to the fields of bioinformatics and inflammatory and autoimmune diseases, with methods of assessing risk of cardiovascular disease or myocardial infarction, and serious infection in patients with inflammatory diseases such as rheumatoid arthritis ("RA"). RA is an example of an inflammatory disease, and is a chronic, systemic autoimmune disorder. It is one of the most common systemic autoimmune diseases worldwide. The immune system of the RA subject targets the subject's joints as well as other organs including the lung, blood vessels and pericardium, leading to inflammation of the joints (arthritis), widespread endothelial inflammation, and even destruction of joint tissue.

There exists a close association between RA and cardiovascular disease (CVD). It is estimated that almost one half of RA-related deaths are a result of CVD and its underlying atherosclerosis, which itself is an inflammatory disorder. The pathogenic features common to both RA and atherosclerosis include pro-inflammatory cytokines, elevated levels of acute phase reactants, neo-angiogenesis, T-cell activation, and leukocyte adhesion molecules, as well as endothelia cell injury. Myocardial infarctions (MI), heart failure, and stroke occur in RA patients at 2 to 4 times the rates as in unaffected individuals.

The most established risk tool developed to estimate an individual's future risk for a CVD event are the Framingham and Reynolds scores. These scores generate 10-year risk scores based on algorithms containing age, gender, cholesterol, blood pressure, and smoking. The Reynolds score further evaluates C-reactive protein (CRP) in generating its 10-year risk score. However, these scores are less effective in predicting individual risk in women and younger individuals, which are groups that are highly represented in RA.

Another issue that complicates the management of RA is the high risk in patients with RA of developing a serious infection(s), especially if the patient is also being treated with corticosteroids. That is, some RA patients are vulnerable to serious infections. Although physicians are cognizant of the risk of serious infection in RA patients in general terms, the high frequency of serious infections in RA patients is not fully appreciated, partly because it is only over a long period of time that this becomes apparent (3-10 years) and more importantly because increasingly the prescribing physician is no longer the physician who takes direct responsibility for the actual treatment of the infections. Often the infection is treated by a general physician or an infectious diseases expert or an internist if the infection is so serious that intensive care unit expertise is required. In the case of serial infections, often it is different generalists or specialists who treat each serious infection episode and thus there is no continuity of care and hence diminished appreciation of the serial or recurrent nature of some infections. Hard decisions about whether to continue immunosuppressive or biologic therapies may not be taken by the treating Rheumatologist or primary care physician as a result of diminished appreciation of the impact of a serious infection. Thus there exists a need to develop a test to assess the vulnerability of a patient with RA to developing a serious infection.

Population-based research in RA studying hard endpoints including hospitalized infection and myocardial infarction (MI) is challenging because the relatively low prevalence of RA and outcome event rates limits statistical power. Administrative data from health plans and payers have high validity for studying large cohorts of patients with RA. While these data sources often lack clinical assessments of RA, results of lab tests that measure RA disease activity may provide objective measurements that can augment claims data.

The MBDA score is a validated tool that quantifies 12 serum protein biomarkers to assess disease activity in adult patients with RA (Curtis J R, et al., *Arthritis Care Res.* 64:1794-803 (2012)). Derivation of these 12 biomarkers is described fully in U.S. Pat. No. 9,200,324, which is hereby fully incorporated by reference in its entirety. Biomarkers can sometimes also be influenced by variables including race, sex, genetics, body mass index, hormones, and environmental factors. The present teachings provide methods for assessing risk of infection and CVD utilizing an RA multi-biomarker disease activity score or a combination of a multi-biomarker disease activity score and other clinical variables.

SUMMARY

The present teachings relate to biomarkers associated with inflammatory disease that can be used to assess infection and CVD risk.

In one embodiment, a method for assessing risk of infection or cardiovascular disease (CVD) in a subject with an inflammatory disease is provided. The method comprises performing at least one immunoassay on a first blood sample from the subject to generate a first dataset comprising protein level data for at least two protein markers, wherein the at least two protein markers comprise at least two markers selected from chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); and, vascular endothelial growth factor A (VEGFA); and determining a risk score from the first dataset using an interpretation function, wherein said risk score predicts the risk of infection or CVD in said subject. In an embodiment, the at least two protein markers comprise CHI3L1; CRP; EGF; IL6; LEP; MMP1; MMP3; RETN; SAA1; TNFRSF1A; VCAM1; and, VEGFA. In an embodiment, the score is compared to a clinical assessment. In an embodiment, the clinical assessment is selected from the group consisting of: a DAS, a DAS28, a DAS28-CRP, a DAS28-ESR, a Sharp score, a tender joint count (TJC), and a swollen joint count (SJC). In an embodiment, the at least one immunoassay comprises a multiplex assay. In an embodiment, performance of the at least one immunoassay comprises: obtaining the first blood sample, wherein the first blood sample comprises the protein markers; contacting the first blood sample with a plurality of distinct reagents; generating a plurality of distinct complexes between the reagents and markers; and detecting the complexes to generate the data. In an embodiment, the interpretation function is based on a predictive model. In an embodiment, the inflammatory disease in rheumatoid arthritis (RA). In an embodiment, the risk of infection is one or more of pneumonia or sepsis and/or the risk of CVD is defined by a composite coronary heart disease (CHD) outcome. In an embodiment, the CHD is one or more of myocardial infarction (MI), percutaneous coronary intervention (PCI), or coronary artery bypass grafting (CABG). In an embodiment, the risk score is combined with at least one test clinical score representing at least one clinical variable. In an embodiment, the at least one clinical score incorporates at least one clinical variable chosen from age, gender, sex, smoking status, adiposity, body mass index (BMI), serum leptin, and race/ethnicity. In an embodiment, the at least one clinical score incorporates age, sex, and race. In an embodiment, the at least one clinical score incorporates age and sex.

In another embodiment, a method for recommending a therapeutic regimen in a subject having an autoimmune disorder is provided. The method comprises a) performing at least one immunoassay on a first blood sample from the first subject to generate a first dataset comprising protein level data for at least two protein markers, wherein the at least two protein markers comprise at least two markers selected from chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); and, vascular endothelial growth factor A (VEGFA); b) determining a risk score from the first dataset using an interpretation function, wherein said risk score predicts the risk of infection or CVD in said first subject; and c) recommending i) no therapy regimen if the score is low: or ii) a therapy regimen if the score is high. In an embodiment, the at least two protein markers comprise CHI3L1; CRP; EGF; IL6; LEP; MMP1; MMP3; RETN; SAA1; TNFRSF1A; VCAM1; and, VEGFA. In an embodiment, the score is compared to a clinical assessment. In an embodiment, the clinical assessment is selected from the group consisting of: a DAS, a DAS28, a DAS28-CRP, a DAS28-ESR, a Sharp score, a tender joint count (TJC), and a swollen joint count (SJC). In an embodiment, the at least one immunoassay comprises a multiplex assay. In an embodiment, performance of the at least one immunoassay comprises: obtaining the first blood sample, wherein the first blood sample comprises the protein markers; contacting the first blood sample with a plurality of distinct reagents; generating a plurality of distinct complexes between the reagents and markers; and detecting the complexes to generate the data. In an embodiment, the interpretation function is based on a predictive model. In an embodiment, the inflammatory disease in rheumatoid arthritis (RA). In an embodiment, the risk of infection is one or more of pneumonia or sepsis and/or the risk of CVD is defined by a composite coronary heart disease (CHD) outcome. In an embodiment, the CHD is one or more of myocardial infarction (MI), percutaneous coronary intervention (PCI), or coronary artery bypass grafting (CABG). In an embodiment, the score is low if on a scale of 1-100, the score is less than or equal to about 30. In an embodiment, the score is high if on a scale of 1-100, the score is greater than about 30. In an embodiment, the score is low if on a scale of 1-100, the score is predictive of flare and the score is less than or equal to about 30. In an embodiment, the score is high if on a scale of 1-100, the score is predictive of flare and the score is greater than about 30. In an embodiment, the risk score is combined with at least one test clinical score representing at least one clinical variable. In an embodiment, the at least one clinical score incorporates at least one clinical variable chosen from age, gender, sex, smoking status, adiposity, body mass index (BMI), serum leptin, and race/ethnicity. In an embodiment, the at least one clinical score incorporates age, sex, and race. In an embodiment, the at least one clinical score incorporates age and sex.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF VARIOUS EMBODIMENTS

Figure 1:
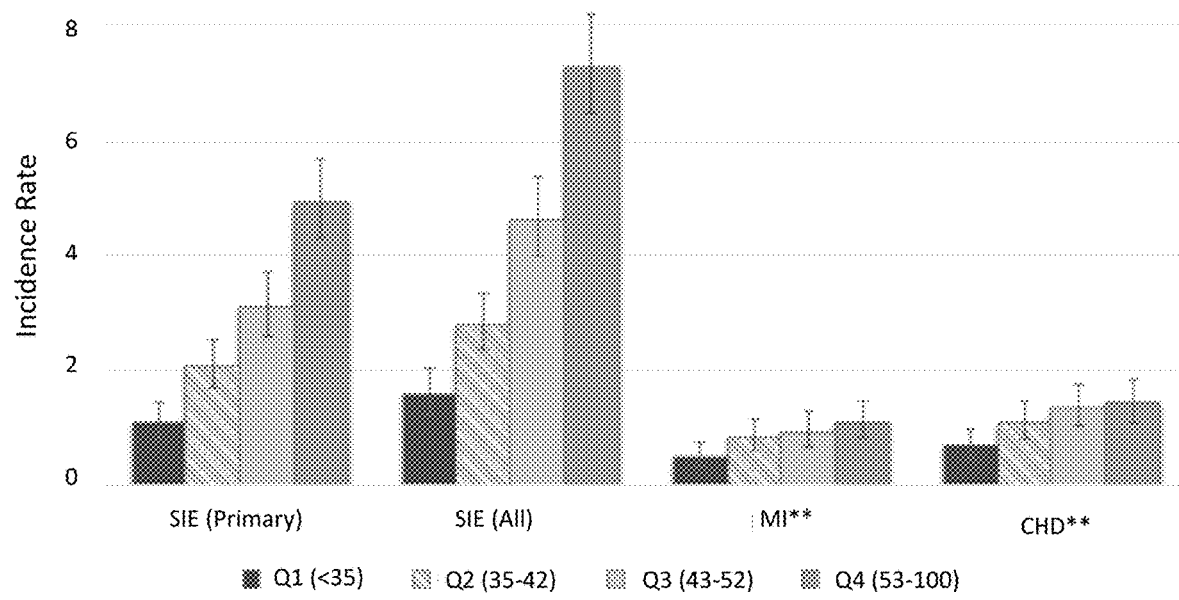
FIG. 1 illustrates incidence rates per 100 patient-years of hospitalized serious infection event (SIE), myocardial infarction (MI), and coronary heart disease (CHD) events by quartile of MBDA. Error bars represent the 95% Cis around the incidence rate. MI and CHD were primary or secondary. SEI is a serious infection event.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to the identification of biomarkers associated with subjects having inflammatory and/or autoimmune diseases, for example RA, and that are useful in determining or assessing infection and/or CVD risk, and in particular, in response to inflammatory disease therapy for recommending optimal therapy.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

Definitions

"Accuracy" refers to the degree that a measured or calculated value conforms to its actual value. "Accuracy" in clinical testing relates to the proportion of actual outcomes (true positives or true negatives, wherein a subject is correctly classified as having disease or as healthy/normal, respectively) versus incorrectly classified outcomes (false positives or false negatives, wherein a subject is incorrectly classified as having disease or as healthy/normal, respectively). Other and/or equivalent terms for "accuracy" can include, for example, "sensitivity," "specificity," "positive predictive value (PPV)," "the AUC," "negative predictive value (NPV)," "likelihood," and "odds ratio." "Analytical accuracy," in the context of the present teachings, refers to the repeatability and predictability of the measurement process. Analytical accuracy can be summarized in such measurements as, e.g., coefficients of variation (CV), and tests of concordance and calibration of the same samples or controls at different times or with different assessors, users, equipment, and/or reagents. See, e.g., R. Vasan, *Circulation* 2006, 113(19):2335-2362 for a summary of considerations in evaluating new biomarkers.

The term "administering" as used herein refers to the placement of a composition into a subject by a method or route that results in at least partial localization of the composition at a desired site such that a desired effect is produced. Routes of administration include both local and systemic administration. Generally, local administration results in more of the composition being delivered to a specific location as compared to the entire body of the subject, whereas, systemic administration results in delivery to essentially the entire body of the subject.

The term "algorithm" encompasses any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, and neural networks trained on populations. Also of use in the context of biomarkers are linear and non-linear equations and statistical classification analyses to determine the relationship between (a) levels of biomarkers detected in a subject sample and (b) the level of the respective subject's infection or CVD risk.

The term "analyte" in the context of the present teachings can mean any substance to be measured, and can encompass biomarkers, markers, nucleic acids, electrolytes, metabolites, proteins, sugars, carbohydrates, fats, lipids, cytokines, chemokines, growth factors, proteins, peptides, nucleic acids, oligonucleotides, metabolites, mutations, variants, polymorphisms, modifications, fragments, subunits, degradation products and other elements. For simplicity, standard gene symbols may be used throughout to refer not only to genes but also gene products/proteins, rather than using the standard protein symbol; e.g., APOA1 as used herein can refer to the gene APOA1 and also the protein ApoAI. In general, hyphens are dropped from analyte names and symbols herein (IL-6=IL6).

To "analyze" includes determining a value or set of values associated with a sample by measurement of analyte levels in the sample. "Analyze" may further comprise and comparing the levels against constituent levels in a sample or set of samples from the same subject or other subject(s). The biomarkers of the present teachings can be analyzed by any of various conventional methods known in the art. Some such methods include but are not limited to: measuring serum protein or sugar or metabolite or other analyte level, measuring enzymatic activity, and measuring gene expression.

The term "antibody" refers to any immunoglobulin-like molecule that reversibly binds to another with the required selectivity. Thus, the term includes any such molecule that is capable of selectively binding to a biomarker of the present teachings. The term includes an immunoglobulin molecule capable of binding an epitope present on an antigen. The term is intended to encompass not only intact immunoglobulin molecules, such as monoclonal and polyclonal antibodies, but also antibody isotypes, recombinant antibodies, bi-specific antibodies, humanized antibodies, chimeric antibodies, anti-idiopathic (anti-ID) antibodies, single-chain antibodies, Fab fragments, F(ab') fragments, fusion protein antibody fragments, immunoglobulin fragments, F, fragments, single chain F, fragments, and chimeras comprising an immunoglobulin sequence and any modifications of the foregoing that comprise an antigen recognition site of the required selectivity.

"Autoimmune disease" encompasses any disease, as defined herein, resulting from an immune response against substances and tissues normally present in the body. Examples of suspected or known autoimmune diseases include rheumatoid arthritis, early rheumatoid arthritis, axial spondyloarthritis, juvenile idiopathic arthritis, seronegative spondyloarthropathies, ankylosing spondylitis, psoriatic arthritis, antiphospholipid antibody syndrome, autoimmune hepatitis, Behçet's disease, bullous pemphigoid, coeliac disease, Crohn's disease, dermatomyositis, Goodpasture's syndrome, Graves' disease, Hashimoto's disease, idiopathic thrombocytopenic purpura, IgA nephropathy, Kawasaki disease, systemic lupus erythematosus, mixed connective tissue disease, multiple sclerosis, myasthenia gravis, polymyositis, primary biliary cirrhosis, psoriasis, scleroderma, Sjögren's syndrome, ulcerative colitis, vasculitis, Wegener's granulomatosis, temporal arteritis, Takayasu's arteritis, Henoch-Schonlein purpura, leucocytoclastic vasculitis, polyarteritis nodosa, Churg-Strauss Syndrome, and mixed cryoglobulinemic vasculitis.

A "biologic" or "biotherapy" or "biopharmaceutical" is a pharmaceutical therapy product manufactured or extracted from a biological substance. A biologic can include vaccines, blood or blood components, allergenics, somatic cells, gene therapies, tissues, recombinant proteins, and living cells; and can be composed of sugars, proteins, nucleic acids, living cells or tissues, or combinations thereof. Examples of biologic drugs can include but are not limited to biological agents that target the tumor necrosis factor (TNF)-alpha molecules and the TNF inhibitors, such as infliximab, adalimumab, etanercept and golimumab. Other classes of biologic drugs include IL1 inhibitors such as anakinra, T-cell modulators such as abatacept, B-cell modulators such as rituximab, and IL6 inhibitors such as tocilizumab.

"Biomarker," "biomarkers," "marker" or "markers" in the context of the present teachings encompasses, without limitation, cytokines, chemokines, growth factors, proteins, peptides, nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers and/or transcript variants. Biomarkers also encompass non-blood borne factors and non-analyte physiological markers of health status, and/or other factors or markers not measured from samples (e.g., biological samples such as bodily fluids), such as clinical parameters and traditional factors for clinical assessments. Biomarkers can also include any indices that are calculated and/or created mathematically. Biomarkers can also include combinations of any one or more of the foregoing measurements, including temporal trends and differences. Where the biomarkers of certain embodiments of the present teachings are proteins, the gene symbols and names used herein are to be understood to refer to the protein products of these genes, and the protein products of these genes are intended to include any protein isoforms of these genes, whether or not such isoform sequences are specifically described herein. Where the biomarkers are nucleic acids, the gene symbols and names used herein are to refer to the nucleic acids (DNA or RNA) of these genes, and the nucleic acids of these genes are intended to include any transcript variants of these genes, whether or not such transcript variants are specifically described herein. Biomarkers can include, but are not limited to the biomarkers described in Tables 1-12 herein.

The term "cardiovascular disease" or "cardiovascular disorder" or "CVD" are terms used to classify numerous conditions affecting the heart, heart valves, and vasculature (e.g., arteries and veins) of the body and encompasses diseases and conditions including, but not limited to arteriosclerosis, atherosclerosis, myocardial infarction (MI), acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease. CVD outcomes can be determined by means such as coronary intervention (PCI), or coronary artery bypass grafting (CABG).

A "clinical assessment," or "clinical datapoint" or "clinical endpoint," in the context of the present teachings can refer to a measure of disease activity or severity. A clinical assessment can include a score, a value, or a set of values that can be obtained from evaluation of a sample (or population of samples) from a subject or subjects under determined conditions. A clinical assessment can also be a questionnaire completed by a subject. A clinical assessment can also be predicted by biomarkers and/or other parameters. One of skill in the art will recognize that the clinical assessment for RA, as an example, can comprise, without limitation, one or more of the following: DAS (defined herein), DAS28, DAS28-ESR, DAS28-CRP, health assessment questionnaire (HAQ), modified HAQ (mHAQ), multi-dimensional HAQ (MDHAQ), visual analog scale (VAS), physician global assessment VAS, patient global assessment VAS, pain VAS, fatigue VAS, overall VAS, sleep VAS, simplified disease activity index (SDAI), clinical disease activity index (CDAI), routine assessment of patient index data (RAPID), RAPID3, RAPID4, RAPID5, American College of Rheumatology (ACR), ACR20, ACR50, ACR70, SF-36 (a well-validated measure of general health status), RA MRI score (RAMRIS; or RA MRI scoring system), total Sharp score (TSS), van der Heijde-modified TSS, van der Heijde-modified Sharp score (or Sharp-van der Heijde score (SHS)), Larsen score, TJC, swollen joint count (SJC), CRP titer (or level), and erythrocyte sedimentation rate (ESR).

The term "clinical variable" or "clinical parameters" in the context of the present teachings encompasses all measures of the health status of a subject. A clinical parameter can be used to derive a clinical assessment of the subject's disease activity. Clinical parameters can include, without limitation: therapeutic regimen (including but not limited to DMARDs, whether conventional or biologics, steroids, etc.), TJC, SJC, morning stiffness, arthritis of three or more joint areas, arthritis of hand joints, symmetric arthritis, rheumatoid nodules, radiographic changes and other imaging, gender/sex, smoking status, age, race/ethnicity, disease duration, diastolic and systolic blood pressure, resting heart rate, height, weight, adiposity, body-mass index, serum leptin, family history, CCP status (i.e., whether subject is positive or negative for anti-CCP antibody), CCP titer, RF status, RF titer, ESR, CRP titer, menopausal status, and whether a smoker/non-smoker.

"Clinical assessment" and "clinical parameter" are not mutually exclusive terms. There may be overlap in members of the two categories. For example, CRP concentration can be used as a clinical assessment of disease activity; or, it can be used as a measure of the health status of a subject, and thus serve as a clinical parameter.

Figure 2:
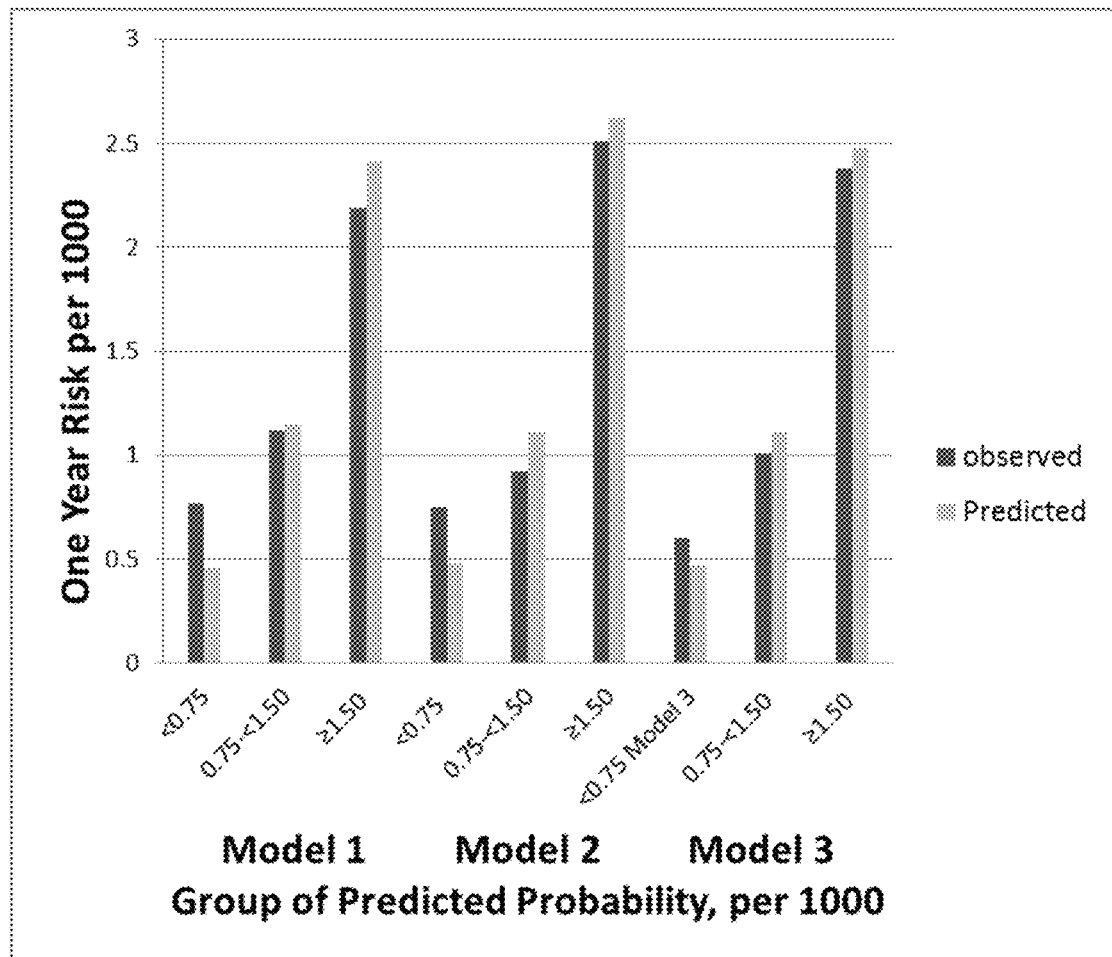
FIG. 2 illustrates risk based on three different models. Model 1 included age, sex and race. Model 2 included age, sex race, 9 comorbidities and CVD medication classes, plus interaction terms. Model 3 included age, sex, and race plus categorized MBDA score.
Figure 3:
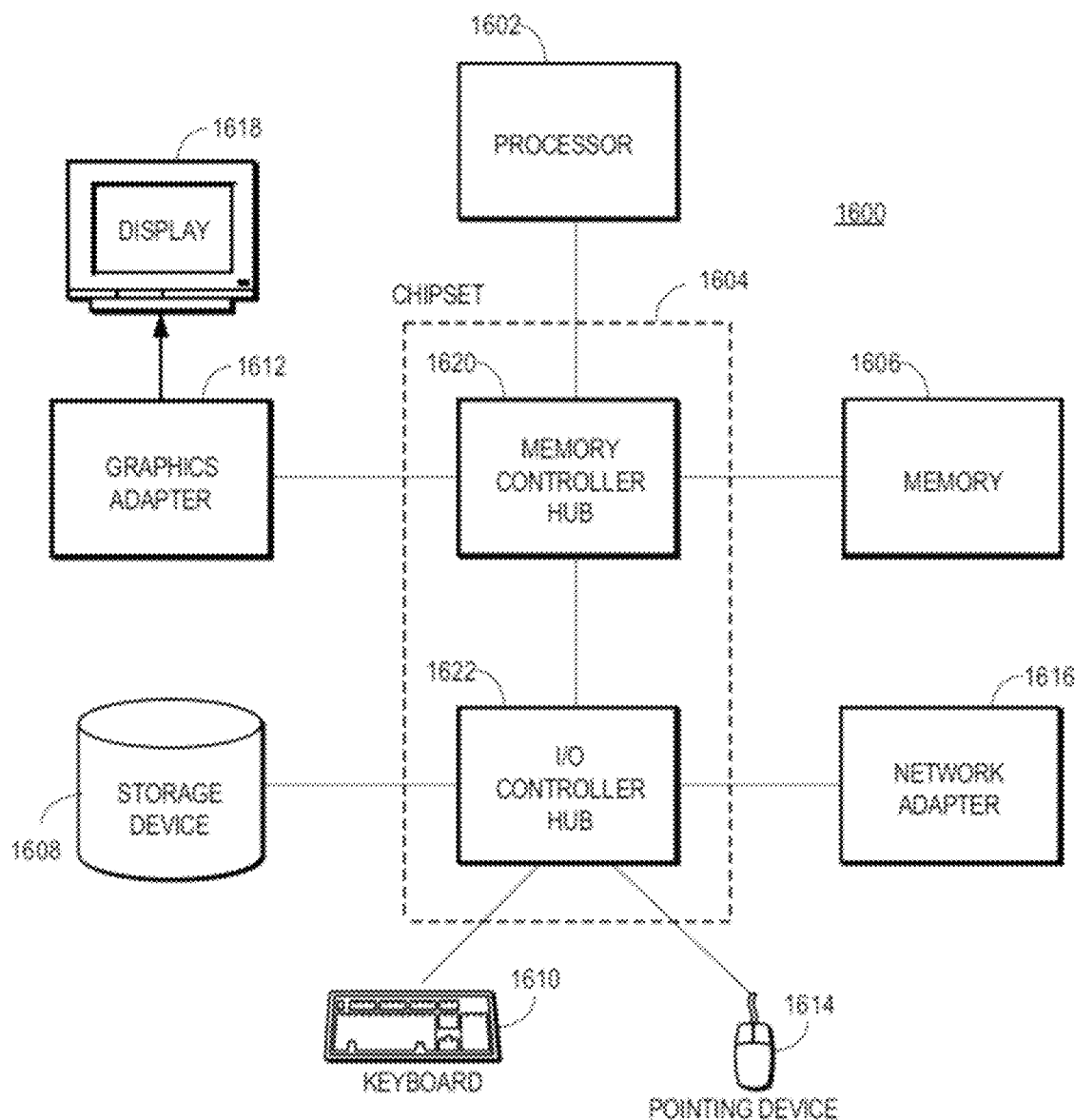
FIG. 3 illustrates a high-level block diagram of a computer (1600). Illustrated are at least one processor (1602) coupled to a chipset (1604). Also coupled to the chipset (1604) are a memory (1606), a storage device (1608), a keyboard (1610), a graphics adapter (1612), a pointing device (1614), and a network adapter (1616). A display (1618) is coupled to the graphics adapter (1612). In one embodiment, the functionality of the chipset (1604) is provided by a memory controller hub 1620) and an I/O controller hub (1622). In another embodiment, the memory (1606) is coupled directly to the processor (1602) instead of the chipset (1604). The storage device 1608 is any device capable of holding data, like a hard drive, compact disk read-only memory (CD-ROM), DVD, or a solid-state memory device. The memory (1606) holds instructions and data used by the processor (1602). The pointing device (1614) may be a mouse, track ball, or other type of pointing device, and is used in combination with the keyboard (1610) to input data into the computer system (1600). The graphics adapter (1612) displays images and other information on the display (1618). The network adapter (1616) couples the computer system (1600) to a local or wide area network.

The term "computer" carries the meaning that is generally known in the art; that is, a machine for manipulating data according to a set of instructions. For illustration purposes only, FIG. 2 is a high-level block diagram of a computer (1600). As is known in the art, a "computer" can have different and/or other components than those shown in FIG. 2. In addition, the computer 1600 can lack certain illustrated components. Moreover, the storage device (1608) can be local and/or remote from the computer (1600) (such as embodied within a storage area network (SAN)). As is known in the art, the computer (1600) is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device (1608), loaded into the memory (1606), and executed by the processor (1602). Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The term "cytokine" in the present teachings refers to any substance secreted by specific cells that can be of the immune system that carries signals between cells and thus has an effect on other cells. The term "cytokines" encompasses "growth factors." "Chemokines" are also cytokines. They are a subset of cytokines that are able to induce chemotaxis in cells; thus, they are also known as "chemotactic cytokines."

"DAS" refers to the Disease Activity Score, a measure of the activity of RA in a subject, well-known to those of skill in the art. See D. van der Heijde et al., *Ann. Rheum. Dis.* 1990, 49(11):916-920. "DAS" as used herein refers to this particular Disease Activity Score. The "DAS28" involves the evaluation of 28 specific joints. It is a current standard well-recognized in research and clinical practice. Because the DAS28 is a well-recognized standard, it may be referred to as "DAS." Although "DAS" may refer to calculations based on 66/68 or 44 joint counts, unless otherwise specified, "DAS" herein will encompass the DAS28. Unless otherwise specified herein, the term "DAS28," as used in the present teachings, can refer to a DAS28-ESR or DAS28-CRP, as obtained by any of the four formulas described above; or, DAS28 can refer to another reliable DAS28 formula as may be known in the art.

A DAS28 can be calculated for an RA subject according to the standard as outlined at the das-score.nl website, maintained by the Department of Rheumatology of the University Medical Centre in Nijmegen, the Netherlands. The number of swollen joints, or swollen joint count out of a total of 28 (SJC28), and tender joints, or tender joint count out of a total of 28 (TJC28) in each subject is assessed. In some DAS28 calculations the subject's general health (GH) is also a factor, and can be measured on a 100 mm Visual Analogue Scale (VAS). GH may also be referred to herein as PG or PGA, for "patient global health assessment" (or merely "patient global assessment"). A "patient global health assessment VAS," then, is GH measured on a Visual Analogue Scale.

"DAS28-CRP" (or "DAS28CRP") is a DAS28 assessment calculated using CRP in place of ESR (see below). CRP is produced in the liver. Normally there is little or no CRP circulating in an individual's blood serum—CRP is generally present in the body during episodes of acute inflammation or infection, so that a high or increasing amount of CRP in blood serum can be associated with acute infection or inflammation. A blood serum level of CRP greater than 1 mg/dL is usually considered high. Most inflammation and infections result in CRP levels greater than 10 mg/dL. The amount of CRP in subject sera can be quantified using, for example, the DSL-10-42100 ACTIVE® US C-Reactive Protein Enzyme-Linked Immunosorbent Assay (ELISA), developed by Diagnostics Systems Laboratories, Inc. (Webster, TX). CRP production is associated with radiological progression in RA. See M. Van Leeuwen et al., *Br. J. Rheum.* 1993, 32(suppl.):9-13). CRP is thus considered an appropriate alternative to ESR in measuring RA disease activity. See R. Mallya et al., *J. Rheum.* 1982, 9(2):224-228, and F. Wolfe, *J. Rheum.* 1997, 24:1477-1485.

The DAS28-CRP can be calculated according to either of the formulas below, with or without the GH factor, where "CRP" represents the amount of this protein present in a subject's blood serum in mg/L, "sqrt" represents the square root, and "ln" represents the natural logarithm:

(a) DAS28-CRP with GH (or DAS28-CRP4)=
$(0.56*\text{sqrt}(TJC28)+0.28*\text{sqrt}(SJC28)+0.36*\ln(CRP+1))+(0.014*GH)+0.96$; or, (b) DAS28-CRP without GH (or DAS28-CRP3)=
$(0.56*\text{sqrt}(TJC28)+0.28*\text{sqrt}(SJC28)+0.36*\ln(CRP+1))*1.10+1.15$.

The "DAS28-ESR" is a DAS28 assessment wherein the ESR for each subject is also measured (in mm/hour). The DAS28-ESR can be calculated according to the formula:

(a) DAS28-ESR with GH (or DAS28-ESR4)=$0.56*\text{sqrt}(TJC28)+0.28*\text{sqrt}(SJC28)+0.70*\ln(ESR)+0.014*GH$; or, (b) DAS28-ESR without GH=$0.56*\text{sqrt}(TJC28)+0.28*\text{sqrt}(SJC28)+0.70*\ln(ESR)*1.08+0.16$.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

A "difference" as used herein refers to an increase or decrease in the measurable expression of a biomarker or panel of biomarkers as compared to the measurable expression of the same biomarker or panel of biomarkers in a second samples.

The term "disease" in the context of the present teachings encompasses any disorder, condition, sickness, ailment, etc. that manifests in, e.g., a disordered or incorrectly functioning organ, part, structure, or system of the body, and results from, e.g., genetic or developmental errors, infection, poisons, nutritional deficiency or imbalance, toxicity, or unfavorable environmental factors.

A DMARD can be conventional or biologic. Examples of DMARDs that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intramuscular gold (IM gold), leflunomide (LEF), levofloxacin (LEV), and sulfasalazine (SSZ). Examples of other conventional DMARDs include, but are not limited to, folinic acid, D-pencillamine, gold auranofin, gold aurothioglucose, gold thiomalate, cyclophosphamide, and chlorambucil. Examples of biologic DMARDs (or biologic drugs) include but are not limited to biological agents that target the tumor necrosis factor (TNF)-alpha molecules such as infliximab, adalimumab, etanercept and golimumab. Other classes of biologic DMARDs include IL1 inhibitors such as anakinra, T-cell modulators such as abatacept, B-cell modulators such as rituximab, and IL6 inhibitors such as tocilizumab.

The term "flare" as used herein is a sudden and severe increase in the onset of symptoms and clinical manifestations including, but not limited to, an increase in SJC, increase in TJC, increase in serologic markers of inflammation (e.g., CRP and ESR), decrease in subject function (e.g., ability to perform basic daily activities), increase in morning stiffness, and increases in pain that commonly lead to therapeutic intervention and potentially to treatment intensification.

An "immunoassay" as used herein refers to a biochemical assay that uses one or more antibodies to measure the presence or concentration of an analyte or biomarker in a biological sample.

The term "infection" or "serious infection" as used herein refers to an infection that leads to death, hospitalization or requires intravenous antibiotics. Serious infections include, but not limited to bacterial infections, *Mycobacterium tuberculosis* and other mycobacterial infections, invasive pneumococcal disease, pneumonia, septicaemia and bacteraemia, invasive bacterial infection after chemotherapy, neonatal septicaemia, meningitis, encephalitis, bone and joint sepsis, severe cutaneous infections including cellulitis, urosepsis, bowel and other GI tract infections, severe viral infections and opportunistic infections, especially fungal infection.

"Inflammatory disease" in the context of the present teachings encompasses, without limitation, any disease, as defined herein, resulting from the biological response of vascular tissues to harmful stimuli, including but not limited to such stimuli as pathogens, damaged cells, irritants, antigens and, in the case of autoimmune disease, substances and tissues normally present in the body. Non-limiting examples of inflammatory disease include rheumatoid arthritis (RA), eRA, ankylosing spondylitis, psoriatic arthritis, atherosclerosis, asthma, autoimmune diseases, chronic inflammation, chronic prostatitis, glomerulonephritis, hypersensitivities, inflammatory bowel diseases, pelvic inflammatory disease, reperfusion injury, transplant rejection, and vasculitis.

"Interpretation function," as used herein, means the transformation of a set of observed data into a meaningful determination of particular interest; e.g., an interpretation function may be a predictive model that is created by utilizing one or more statistical algorithms to transform a dataset of observed biomarker data into a meaningful determination of disease activity, CVD or infection risk, or the disease state of a subject.

"Measuring" or "measurement" in the context of the present teachings refers to determining the presence, absence, quantity, amount, or effective amount of a substance in a clinical or subject-derived sample, including the concentration levels of such substances, or evaluating the values or categorization of a subject's clinical parameters.

A "multiplex assay" as used herein refers to an assay that simultaneously measures multiple analytes, e.g., protein analytes, in a single run or cycle of the assay.

A "multi-biomarker disease activity index score," "MBDA score," or simply "MBDA," in the context of the present teachings, is a score that provides a quantitative measure of inflammatory disease activity or the state of inflammatory disease in a subject. A set of data from particularly selected biomarkers, such as from the disclosed set of biomarkers, is input into an interpretation function according to the present teachings to derive the MBDA score. The interpretation function, in some embodiments, can be created from predictive or multivariate modeling based on statistical algorithms. Input to the interpretation function can comprise the results of testing two or more of the disclosed set of biomarkers, alone or in combination with clinical parameters and/or clinical assessments, also described herein. In some embodiments of the present teachings, the MBDA score is a quantitative measure of autoimmune disease activity. In some embodiments, the MBDA score is a quantitative measure of RA disease activity. MBDA as used herein can refer to a VECTRA® DA score. As used herein the teachings allow an MBDA score to be used to determine infection and/or CVD risk.

The terms "normal," "control," and "healthy," as used herein, refer generally to a subject or individual who does not have, is not/has not been diagnosed with, or is asymptomatic for a particular disease or disorder. The terms can also refer to a sample obtained from such subject or individual. The disease or disorder under analysis or comparison is determinative of whether the subject is a "control" in that situation. By example, where the level of a particular serum marker is obtained from an individual known to have RA, but who is not diagnosed with and is asymptomatic for CVD, that subject can be the "RA subject." The level of the marker thus obtained from the RA subject can be compared to the level of that same marker from a subject who is diagnosed with RA, but who is known not to have prevalent CVD and not to be a CVD progressor; i.e., a "normal subject." Thus, "normal" in this example refers to the subject's CVD status, not RA status.

"Performance" in the context of the present teachings relates to the quality and overall usefulness of, e.g., a model, algorithm, or diagnostic or prognostic test. Factors to be considered in model or test performance include, but are not limited to, the clinical and analytical accuracy of the test, use characteristics such as stability of reagents and various components, ease of use of the model or test, health or economic value, and relative costs of various reagents and components of the test. Performing can mean the act of carrying out a function.

A "population" is any grouping of subjects of like specified characteristics. The grouping could be according to, for example but without limitation, clinical parameters, clinical assessments, therapeutic regimen, disease status (e.g. with disease or healthy), level of disease activity, level of infection or CVD risk, etc. In the context of using the MBDA score in comparing risk between populations, an aggregate value can be determined based on the observed MBDA scores of the subjects of a population; e.g., at particular timepoints in a longitudinal study. The aggregate value can be based on, e.g., any mathematical or statistical formula useful and known in the art for arriving at a meaningful aggregate value from a collection of individual datapoints; e.g., mean, median, median of the mean, etc.

A "predictive model," which term may be used synonymously herein with "multivariate model" or simply a "model," is a mathematical construct developed using a statistical algorithm or algorithms for classifying sets of data. The term "predicting" refers to generating a value for a datapoint without actually performing the clinical diagnostic procedures normally or otherwise required to produce that datapoint; "predicting" as used in this modeling context should not be understood solely to refer to the power of a model to predict a particular outcome. Predictive models can provide an interpretation function; e.g., a predictive model can be created by utilizing one or more statistical algorithms or methods to transform a dataset of observed data into a meaningful determination of a risk score or the disease state of a subject. See Calculation of the MBDA score for some examples of statistical tools useful in model development.

A "prognosis" is a prediction as to the likely outcome of a disease. Prognostic estimates are useful in, e.g., determining an appropriate therapeutic regimen for a subject.

A "quantitative dataset" or "quantitative data" as used in the present teachings, refers to the data derived from, e.g., detection and composite measurements of expression of a plurality of biomarkers (i.e., two or more) in a subject sample. The quantitative dataset can be used to generate a score for the identification, monitoring and treatment of disease states, and in characterizing the biological condition of a subject. It is possible that different biomarkers will be detected depending on the disease state or physiological condition of interest.

"Recommending" as used herein refers to making a recommendation for a therapeutic regimen or excluding (i.e., not recommending) a certain therapeutic regimen for a subject. Such a recommendation shall serve optionally together with other information as a basis for a clinician to apply a certain therapeutic regimen for an individual subject.

The term "remission" refers to the state of absence of disease activity in patients known to have a chronic illness that usually cannot be cured. The term "sustained clinical remission" or "SC-REM" as used herein refers to a state of clinical remission sustained as evaluated based on clinical assessments, for example, DAS28 for at least six months. The term "functional remission" as used herein refers to a state of remission as evaluated using functional assessment measures such as but not limited to HAQ. Sustained remission can be used interchangeably with maintained remission.

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including synovial fluid, gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

A "score" is a value or set of values selected so as to provide a quantitative measure of a variable or characteristic of a subject's condition, and/or to discriminate, differentiate or otherwise characterize a subject's condition. The value(s) comprising the score can be based on, for example, quantitative data resulting in a measured amount of one or more sample constituents obtained from the subject, or from clinical parameters, or from clinical assessments, or any combination thereof. In certain embodiments the score can be derived from a single constituent, parameter or assessment, while in other embodiments the score is derived from multiple constituents, parameters and/or assessments. The score can be based upon or derived from an interpretation function; e.g., an interpretation function derived from a particular predictive model using any of various statistical algorithms known in the art. A "change in score" can refer to the absolute change in score, e.g., from one time point to the next, or the percent change in score, or the change in the score per unit time (e.g., the rate of score change). The term "risk score" as used herein generally refers to an indicator for the risk of having an infection or CVD. The risk score provides an estimate of the likelihood of having an infection or CVD. Thus, in the context of the present invention, the risk score, refers to predicting the risk or acquiring or not acquiring an infection, or acquiring or not acquiring CVD.

A "multiplex assay" as used herein refers to an assay that simultaneously measures multiple analytes, e.g., protein analytes, in a single run or cycle of the assay.

"Statistically significant" in the context of the present teachings means an observed alteration is greater than what would be expected to occur by chance alone (e.g., a "false positive"). Statistical significance can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered highly significant (not random chance) at a p-value less than or equal to 0.05.

A "subject" in the context of the present teachings is generally a mammal. The subject can be a patient. The term "mammal" as used herein includes but is not limited to a human, non-human primate, dog, cat, mouse, rat, cow, horse, and pig. Mammals other than humans can be advantageously used as subjects that represent animal models of inflammation. A subject can be male or female. A subject can be one who has been previously diagnosed or identified as having an inflammatory disease. A subject can be one who has already undergone, or is undergoing, a therapeutic intervention for an inflammatory disease. A subject can also be one who has not been previously diagnosed as having an inflammatory disease; e.g., a subject can be one who exhibits one or more symptoms or risk factors for an inflammatory condition, or a subject who does not exhibit symptoms or risk factors for an inflammatory condition, or a subject who is asymptomatic for inflammatory disease.

A "therapeutic regimen," "therapy" or "treatment(s)," as described herein, includes all clinical management of a subject and interventions, whether biological, chemical, physical, or a combination thereof, intended to sustain, ameliorate, improve, or otherwise alter the condition of a subject. These terms may be used synonymously herein. Treatments include but are not limited to administration of prophylactics or therapeutic compounds (including conventional DMARDs, biologic DMARDs, non-steroidal anti-inflammatory drugs (NSAID's) such as COX-2 selective inhibitors, and corticosteroids), exercise regimens, physical therapy, dietary modification and/or supplementation, bariatric surgical intervention, administration of pharmaceuticals and/or anti-inflammatories (prescription or over-the-counter), and any other treatments known in the art as efficacious in preventing, delaying the onset of, or ameliorating disease. A "response to treatment" includes a subject's response to any of the above-described treatments, whether biological, chemical, physical, or a combination of the foregoing. A "treatment course" relates to the dosage, duration, extent, etc. of a particular treatment or therapeutic regimen. An initial therapeutic regimen as used herein is the first line of treatment.

A "time point" as used herein refers to a manner of describing a time, which can be substantially described with a single point. A time point may also be described as a time range of a minimal unit which can be detected. A time point can refer to a state of the aspect of a time or a manner of description of a certain period of time. Such a time point or range can include, for example, an order of seconds, minutes to hours, or days.

Use of the Present Teachings in Predicting Infection and CVD Risk

In embodiments of the present teachings, an MBDA score can be used to predict risk of infection and CVD.

Diseases and Medical Conditions

Diseases and medical conditions of the invention can include rheumatoid arthritis (RA) and cardiovascular diseases (CVDs). CVDs can include atherosclerosis, coronary atherosclerosis, carotid atherosclerosis, hypertension (e.g., pulmonary hypertension, labile hypertension, idiopathic hypertension, low-renin hypertension, salt-sensitive hypertension, low-renin hypertension, thromboembolic pulmonary hypertension, pregnancy-induced hypertension, renovascular hypertension, hypertension-dependent end-stage renal disease, hypertension associated with cardiovascular surgical procedures, and hypertension with left ventricular (LV) hypertrophy), LV diastolic dysfunction, unobstructive coronary heart diseases, myocardial infarctions, cerebral infarctions, peripheral vascular disease, cerebrovascular disease, cerebral ischemia, angina (including chronic, stable, unstable and variant (Prinzmetal) angina pectoris), aneurysm, ischemic heart disease, thrombosis, platelet aggregation, platelet adhesion, smooth muscle cell proliferation, vascular or non-vascular complications associated with the use of medical devices, wounds associated with the use of medical devices, vascular or non-vascular wall damage, peripheral vascular disease, neointimal hyperplasia following percutaneous transluminal coronary angiography, vascular grafting, coronary artery bypass surgery, thromboembolic events, post-angioplasty restenosis, coronary plaque inflammation, hypercholesterolemia, hypertriglyceridemia, embolism, stroke, shock, arrhythmia, atrial fibrillation or atrial flutter, thrombotic occlusion and reclusion cerebrovascular incidents, left ventricular dysfunction, cardiac hypertrophy, and hypertension with left ventricular hypertrophy and/or unobstructive CVD. Infections can include sepsis and pneumonia, and other serious infection events (SIE) known to a skilled practitioner.

In other embodiments, CVD can include conditions associated with oxidative stress, microvascular coronary heart disease, coronary endothelial dysfunction, left ventricular hypertrophy, dyspnea, inflammation, diabetes, and chronic renal failure. Other CVDs and relevant medical conditions are generally known to one of ordinary skill in the art.

Methods of clinically diagnosing diseases and medical conditions are generally well-known to one of skill in the art. In some embodiments, ultrasound measurements of carotid artery intima-media thickness (IMT) can be used as a measurement of a CVD, e.g., atherosclerosis, and/or as a surrogate endpoint for determining regression or progression of atherosclerotic CVD, especially carotid atherosclerosis. Carotid IMT (CIMT) measures the thickness of carotid artery walls to detect the presence of atherosclerosis (or atherosclerosis burden) and progression of atherosclerosis, and is a surrogate endpoint for evaluating the presence and progression of atherosclerotic CVD. Carotid IMT measurements may be obtained from one or more segments of the carotid artery: in the common carotid, at the bifurcation, or in the internal carotid artery. The IMT of the common carotid artery (CCA), in particular, is useful as an atherosclerosis risk marker. (See, e.g., E. Vicenzini et al., *J. Ultrasound Med.* 2007, 26:427-432.) Atherosclerosis burden within the artery, as measured by carotid IMT, is related to CVD risk, and has been shown to predict fatal coronary death. See, e.g., J T Salonen and R. Salonen, Arterioscler. Thromb. 1991, 11: 1245-1249; L E Chambless et al., *Am. J. Epidemiol.* 1997, 146: and, H N Hodis et al., *Ann. Intern. Med.* 1998, 128: 262-269 (absolute intima-media thickness related to risk for clinical coronary events). Carotid IMT measurements, therefore, can be used to determine atherosclerosis burden in a subject, and changes in IMT can also be used to evaluate changes in atherosclerosis burden, and atherosclerosis progression Biomarkers useful for deriving a MBDA score can include, but are not limited to: chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); and, vascular endothelial growth factor A (VEGFA).

Rating Risk

In some embodiments of the present teachings, the MBDA score, derived as described herein, can be used to predict infection or CVD risk; e.g., as high, medium or low. The score can be varied based on a set of values chosen by the practitioner. For example, a score can be set such that a value is given a range from 0-100, and a difference between two scores would be a value of at least one point. The practitioner can then assign risk based on the values. For example, in some embodiments a score of about 1 to 29 represents a low level of risk, a score of about 30 to 44 represents a moderate level of risk, and a score of about 45 to 100 represents a high level of risk. In some embodiments on a scale of 1-100 a score of ≤38 can represent a low or lower risk, and a score of >38 can represent a high or higher risk. In some embodiments on a scale of 1-100 a score of ≤30 can represent a low or lower risk, and a score of >30 can represent a high or higher risk. In some embodiments, an MBDA scores of about ≤25 is remission, about 26-29 is low, about 30-44 is moderate, and about >44 is high. The cutoffs can vary. For example, in some embodiments a low score can be a score of <30, although for other utilities, a low score can be a score of <29 or <31.

The risk score can also change based on the range of the score. For example a score of 1 to 58 can represent a low level of risk when a range of 0-200 is utilized. Differences can be determined based on the range of score possibilities. For example, if using a score range of 0-100, a small difference in scores can be a difference of about 1, 2, 3, 4, 5, 6, 7, 8, 9, or 10 points; a moderate difference in scores can be a difference of about 4, 5, 6, 7, 8, 9, 10, 11, 12, 13, 14, 15, 16, 17, 18, 19, 20, 21, 22, 23, 24, 25, 26, 27, 28, 29, or 30 points; and large differences can be a change in about 14, 15, 16, 17, 18, 19, 20, 21, 22, 23, 24, 25, 26, 27, 28, 29, 30, 35, 40, 45, or 50 points. Thus, by way of example, a practitioner can define a small difference in scores as about ≤6 points, a moderate difference in scores as about 7-20 points, and a large difference in scores as about >20 points. The difference can be expressed by any unit, for example, percentage points. For example, a practitioner can define a small difference as about ≤6 percentage points, moderate difference as about 7-20 percentage points, and a large difference as about >20 percentage points.

Calculation of Scores

In some embodiments of the present teachings, risk in a subject is measured by: determining the levels in inflammatory disease subject serum of two or more biomarkers, then applying an interpretation function to transform the biomarker levels into a single MBDA score, which provides a quantitative measure of risk in the subject.

In some embodiments, the interpretation function is based on a predictive model. Established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Logistic Regression is the traditional predictive modeling method of choice for dichotomous response variables; e.g., treatment 1 versus treatment 2. It can be used to model both linear and non-linear aspects of the data variables and provides easily interpretable odds ratios.

Discriminant Function Analysis (DFA) uses a set of analytes as variables (roots) to discriminate between two or more naturally occurring groups. DFA is used to test analytes that are significantly different between groups. A forward step-wise DFA can be used to select a set of analytes that maximally discriminate among the groups studied. Specifically, at each step all variables can be reviewed to determine which will maximally discriminate among groups. This information is then included in a discriminative function, denoted a root, which is an equation consisting of linear combinations of analyte concentrations for the prediction of group membership. The discriminatory potential of the final equation can be observed as a line plot of the root values obtained for each group. This approach identifies groups of analytes whose changes in concentration levels can be used to delineate profiles, diagnose and assess therapeutic efficacy. The DFA model can also create an arbitrary score by which new subjects can be classified as either "healthy" or "diseased." To facilitate the use of this score for the medical community the score can be rescaled so a value of 0 indicates a healthy individual and scores greater than 0 indicate increasing risk.

Classification and regression trees (CART) perform logical splits (if/then) of data to create a decision tree. All observations that fall in a given node are classified according to the most common outcome in that node. CART results are easily interpretable—one follows a series of if/then tree branches until a classification results.

Support vector machines (SVM) classify objects into two or more classes. Examples of classes include sets of treatment alternatives, sets of diagnostic alternatives, or sets of prognostic alternatives. Each object is assigned to a class based on its similarity to (or distance from) objects in the training data set in which the correct class assignment of each object is known. The measure of similarity of a new object to the known objects is determined using support vectors, which define a region in a potentially high dimensional space (>R6).

The process of bootstrap aggregating, or "bagging," is computationally simple. In the first step, a given dataset is randomly resampled a specified number of times (e.g., thousands), effectively providing that number of new datasets, which are referred to as "bootstrapped resamples" of data, each of which can then be used to build a model. Then, in the example of classification models, the class of every new observation is predicted by the number of classification models created in the first step. The final class decision is based upon a "majority vote" of the classification models; i.e., a final classification call is determined by counting the number of times a new observation is classified into a given group, and taking the majority classification (33%+ for a three-class system). In the example of logistical regression models, if a logistical regression is bagged 1000 times, there will be 1000 logistical models, and each will provide the probability of a sample belonging to class 1 or 2.

Curds and Whey (CW) using ordinary least squares (OLS) is another predictive modeling method. See L. Breiman and J H Friedman, *J. Royal. Stat. Soc. B* 1997, 59(1):3-54. This method takes advantage of the correlations between response variables to improve predictive accuracy, compared with the usual procedure of performing an individual regression of each response variable on the common set of predictor variables X. In CW, Y=XB*S, where Y=($y_{kj}$) with k for the $k^{th}$ patient and j for $j^{th}$ response (j=1 for TJC, j=2 for SJC, etc.), B is obtained using OLS, and S is the shrinkage matrix computed from the canonical coordinate system. Another method is Curds and Whey and Lasso in combination (CW-Lasso). Instead of using OLS to obtain B, as in CW, here Lasso is used, and parameters are adjusted accordingly for the Lasso approach.

Many of these techniques are useful either combined with a biomarker selection technique (such as, for example, forward selection, backwards selection, or stepwise selection), or for complete enumeration of all potential panels of a given size, or genetic algorithms, or they can themselves include biomarker selection methodologies in their own techniques. These techniques can be coupled with information criteria, such as Akaike's Information Criterion (AIC), Bayes Information Criterion (BIC), or cross-validation, to quantify the tradeoff between the inclusion of additional biomarkers and model improvement, and to minimize overfit. The resulting predictive models can be validated in other studies, or cross-validated in the study they were originally trained in, using such techniques as, for example, Leave-One-Out (LOO) and 10-Fold cross-validation (10-Fold CV).

One example of an interpretation function that provides a MBDA score, derived from a statistical modeling method as described above, is given by the following function:

$$MBDA=(BM1\text{conc}*(0.39^\wedge 0.5)+BM2\text{conc}*(0.39^\wedge 0.5)+BM3\text{conc}*(0.39^\wedge 0.5)+BM4\text{conc}*(0.36^\wedge 0.5)+BM5\text{conc}*(0.31^\wedge 0.5))/10$$

MBDA scores thus obtained for RA subjects with known clinical assessments (e.g., DAS28 scores) can then be compared to those known assessments to determine the level of correlation between the two assessments, and hence determine the accuracy of the MBDA score and its underlying predictive model.

In some embodiments of the present teachings, it is not required that the MBDA score be compared to any predetermined "reference," "normal," "control," "standard,"

"healthy," "pre-disease" or other like index, in order for the MBDA score to provide a quantitative measure of risk in the subject.

In other embodiments of the present teachings, the amount of the biomarker(s) can be measured in a sample and used to derive a MBDA score, which MBDA score is then compared to a "normal" or "control" level or value, utilizing techniques such as, e.g., reference or discrimination limits or risk defining thresholds, in order to define cut-off points and/or abnormal values for infection or CVD risk. The normal level then is the level of one or more biomarkers or combined biomarker indices typically found in a subject who is not suffering from the inflammatory disease under evaluation. Other terms for "normal" or "control" are, e.g., "reference," "index," "baseline," "standard," "healthy," "pre-disease," etc. Such normal levels can vary, based on whether a biomarker is used alone or in a formula combined with other biomarkers to output a score. Alternatively, the normal level can be a database of biomarker patterns from previously tested subjects who did not convert to the inflammatory disease under evaluation over a clinically relevant time period. Reference (normal, control) values can also be derived from, e.g., a control subject or population whose risk is known. In some embodiments of the present teachings, the reference value can be derived from one or more subjects who have been exposed to treatment for disease, or from one or more subjects who are at low risk, or from subjects who have shown improvements as a result of exposure to treatment. In some embodiments the reference value can be derived from one or more subjects who have not been exposed to treatment; for example, samples can be collected from (a) subjects who have received initial treatment, and (b) subjects who have received subsequent treatment, to monitor the progress of the treatment. A reference value can also be derived from risk algorithms or computed indices from population studies.

Measurement of Biomarkers

The quantity of one or more biomarkers of the present teachings can be indicated as a value. The value can be one or more numerical values resulting from the evaluation of a sample, and can be derived, e.g., by measuring level(s) of the biomarker(s) in a sample by an assay performed in a laboratory, or from dataset obtained from a provider such as a laboratory, or from a dataset stored on a server. Biomarker levels can be measured using any of several techniques known in the art. The present teachings encompass such techniques, and further include all subject fasting and/or temporal-based sampling procedures for measuring biomarkers.

The actual measurement of levels of the biomarkers can be determined at the protein or nucleic acid level using any method known in the art. "Protein" detection comprises detection of full-length proteins, mature proteins, pre-proteins, polypeptides, isoforms, mutations, variants, post-translationally modified proteins and variants thereof, and can be detected in any suitable manner. Levels of biomarkers can be determined at the protein level, e.g., by measuring the serum levels of peptides encoded by the gene products described herein, or by measuring the enzymatic activities of these protein biomarkers. Such methods are well-known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Using sequence information provided by the public database entries for the biomarker, expression of the biomarker can be detected and measured using techniques well-known to those of skill in the art. For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

As an example, Northern hybridization analysis using probes which specifically recognize one or more of these sequences can be used to determine gene expression. Alternatively, expression can be measured using RT-PCR; e.g., polynucleotide primers specific for the differentially expressed biomarker mRNA sequences reverse-transcribe the mRNA into DNA, which is then amplified in PCR and can be visualized and quantified. Biomarker RNA can also be quantified using, for example, other target amplification methods, such as TMA, SDA, and NASBA, or signal amplification methods (e.g., bDNA), and the like. Ribonuclease protection assays can also be used, using probes that specifically recognize one or more biomarker mRNA sequences, to determine gene expression.

Alternatively, biomarker protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. See WO 04/056456 and WO 04/088309, each of which is hereby incorporated by reference in its entirety. In this regard, other biomarker analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other biomarker metabolites can be similarly detected using reagents that are specifically designed or tailored to detect such metabolites.

In some embodiments, a biomarker is detected by contacting a subject sample with reagents, generating complexes of reagent and analyte, and detecting the complexes. Examples of "reagents" include but are not limited to nucleic acid primers and antibodies.

In some embodiments of the present teachings an antibody binding assay is used to detect a biomarker; e.g., a sample from the subject is contacted with an antibody reagent that binds the biomarker analyte, a reaction product (or complex) comprising the antibody reagent and analyte is generated, and the presence (or absence) or amount of the complex is determined. The antibody reagent useful in detecting biomarker analytes can be monoclonal, polyclonal, chimeric, recombinant, or a fragment of the foregoing, as discussed in detail above, and the step of detecting the reaction product can be carried out with any suitable immunoassay. The sample from the subject is typically a biological fluid as described above, and can be the same sample of biological fluid as is used to conduct the method described above.

Immunoassays carried out in accordance with the present teachings can be homogeneous assays or heterogeneous assays. Immunoassays carried out in accordance with the present teachings can be multiplexed. In a homogeneous assay the immunological reaction can involve the specific antibody (e.g., anti-biomarker protein antibody), a labeled analyte, and the sample of interest. The label produces a signal, and the signal arising from the label becomes modified, directly or indirectly, upon binding of the labeled analyte to the antibody. Both the immunological reaction of binding, and detection of the extent of binding, can be carried out in a homogeneous solution. Immunochemical labels which can be employed include but are not limited to free radicals, radioisotopes, fluorescent dyes, enzymes, bacteriophages, and coenzymes. Immunoassays include competition assays.

In a heterogeneous assay approach, the reagents can be the sample of interest, an antibody, and a reagent for producing a detectable signal. Samples as described above can be used. The antibody can be immobilized on a support, such as a bead (such as protein A and protein G agarose beads), plate or slide, and contacted with the sample suspected of containing the biomarker in liquid phase. The support is separated from the liquid phase, and either the support phase or the liquid phase is examined using methods known in the art for detecting signal. The signal is related to the presence of the analyte in the sample. Methods for producing a detectable signal include but are not limited to the use of radioactive labels, fluorescent labels, or enzyme labels. For example, if the antigen to be detected contains a second binding site, an antibody which binds to that site can be conjugated to a detectable (signal-generating) group and added to the liquid phase reaction solution before the separation step. The presence of the detectable group on the solid support indicates the presence of the biomarker in the test sample. Examples of suitable immunoassays include but are not limited to oligonucleotides, immunoblotting, immunoprecipitation, immunofluorescence methods, chemiluminescence methods, electrochemiluminescence (ECL), and/or enzyme-linked immunoassays (ELISA).

Those skilled in the art will be familiar with numerous specific immunoassay formats and variations thereof which can be useful for carrying out the method disclosed herein. See, e.g., E. Maggio, *Enzyme-Immunoassay* (1980), CRC Press, Inc., Boca Raton, FL. See also U.S. Pat. No. 4,727,022 to C. Skold et al., titled "Novel Methods for Modulating Ligand-Receptor Interactions and their Application"; U.S. Pat. No. 4,659,678 to GC Forrest et al., titled "Immunoassay of Antigens"; U.S. Pat. No. 4,376,110 to GS David et al., titled "Immunometric Assays Using Monoclonal Antibodies"; U.S. Pat. No. 4,275,149 to D. Litman et al., titled "Macromolecular Environment Control in Specific Receptor Assays"; U.S. Pat. No. 4,233,402 to E. Maggio et al., titled "Reagents and Method Employing Channeling"; and, U.S. Pat. No. 4,230,797 to R. Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein can likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies may also be useful for detecting post-translational modifications of biomarkers. Examples of post-translational modifications include, but are not limited to tyrosine phosphorylation, threonine phosphorylation, serine phosphorylation, citrullination and glycosylation (e.g., O-GlcNAc). Such antibodies specifically detect the phosphorylated amino acids in a protein or proteins of interest, and can be used in the immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF). See U. Wirth et al., *Proteomics* 2002, 2(10): 1445-1451.

Therapeutic Regimens

The present invention provides methods of recommending therapeutic regimens, including withdrawal from therapeutic regiments, following the determination of differences in expression of the biomarkers disclosed herein. Measuring scores derived from expression levels of the biomarkers disclosed herein over a period time can provide a clinician with a dynamic picture of a subject's biological state. These embodiments of the present teachings thus will provide subject-specific biological information, which will be informative for therapy decision and will facilitate therapy response monitoring, and should result in more rapid and more optimized treatment, better control of disease, and an increase in the proportion of subjects achieving remission.

Treatment strategies for infections or CVD for patients with autoimmune disorders are confounded by the fact that some autoimmune disorders, such as RA, is a classification given to a group of subjects with a diverse array of related symptoms that can flare or go into remission. This suggests that certain subtypes of RA are driven by specific cell type or cytokine. As a likely consequence, no single therapy has proven optimal for treatment. Given the increasing numbers of therapeutic options available, the need for an individually tailored treatment directed by immunological prognostic factors of treatment outcome is imperative.

In some embodiments, prediction of infection or CVD risk, in particular in RA patients, who can successfully withdrawal from or discontinue therapy, can be based on a MBDA score. In some embodiments, a high MBDA score as described herein at baseline can be an independent predictor of risk within a certain period of time following discontinuation of therapy. In some embodiments, a moderate MBDA score as described herein at baseline can be an independent predictor of risk within a certain period of time following discontinuation of therapy. In some embodiments, a low MBDA score as described herein at baseline can be an independent predictor of risk, or remission, within a certain period of time following discontinuation of therapy.

Reference Standards for Treatment

In many embodiments, the levels of one or more analyte biomarkers or the levels of a specific panel of analyte biomarkers in a sample are compared to a reference standard ("reference standard" or "reference level") in order to direct treatment decisions. Expression levels of the one or more biomarkers can be combined into a score, which can represent risk. The reference standard used for any embodiment disclosed herein may comprise average, mean, or median levels of the one or more analyte biomarkers or the levels of the specific panel of analyte biomarkers in a control population. The reference standard may further include an earlier time point for the same subject. For example, a reference standard may include a first time point, and the levels of the one or more analyte biomarkers can be examined again at second, third, fourth, fifth, sixth time points, etc. Any time point earlier than any particular time point can be considered a reference standard. The reference standard may additionally comprise cutoff values or any other statistical attribute of the control population, or earlier time points of the same subject, such as a standard deviation from the mean levels of the one or more analyte biomarkers or the levels of the specific panel of analyte biomarkers. In some embodiments, the control population may comprise healthy individuals or the same subject prior to the administration of any therapy.

In some embodiments, a score may be obtained from the reference time point, and a different score may be obtained from a later time point. A first time point can be when an initial therapeutic regimen is begun. A first time point can also be when a first immunoassay is performed. A time point can be hours, days, months, years, etc. In some embodiments, a time point is one month. In some embodiments, a time point is two months. In some embodiments, a time point is three months. In some embodiments, a time point is four months. In some embodiments, a time point is five months. In some embodiments, a time point is six months. In some embodiments, a time point is seven months. In some embodiments, a time point is eight months. In some embodiments, a time point is nine months. In some embodiments, a time point is ten months. In some embodiments, a time point is eleven months. In some embodiments, a time point is twelve months. In some embodiments, a time point is two years. In some embodiments, a time point is three years. In some embodiments, a time point is four years. In some embodiments, a time point is five years. In some embodiments, a time point is ten years.

A difference in the score can be interpreted as a decrease in risk. For example, lower score can indicate a lower level of risk. In these circumstances a second score having a lower score than the reference score, or first score, means that the subject's risk has been lowered (improved) between the first and second time periods. Alternatively, a higher score can indicate a lower level of risk. In these circumstances, a second score having a higher score than the reference score, or first score, also means that the subject's risk has improved between the first and second time periods.

A difference in the score can also be interpreted as an increase in risk. For example, lower score can indicate a higher level of risk. In these circumstances a second score having a lower score than the reference score, or first score, means that the subject's risk has been increased (worsened) between the first and second time periods. Alternatively, a higher score can indicate a higher level of risk. In these circumstances, a second score having a higher score than the reference score, or first score, also means that the subject's risk has worsened between the first and second time periods.

The differences can be variable. For example, when a difference in the score is interpreted as a decrease in risk, a large difference can mean a greater decrease in risk than a lower or moderate difference. Alternatively, when a difference in the score is interpreted as an increase in risk, a large difference can mean a greater increase in risk than a lower or moderate difference.

Reference Therapy for Treatment

In some embodiments, a patient is treated more or less aggressively than a reference therapy based on the difference of scores. A reference therapy is any therapy that is the standard of care for treatment. The standard of care can vary temporally and geographically, and a skilled person can easily determine the appropriate standard of care by consulting the relevant medical literature.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Treatment of Infection or CVD

In one embodiment, the practitioner discontinues a therapy regimen if a score is low. In one embodiment, the practitioner does not change the therapy regimen if the score is high. In one embodiment, the practitioner adjusts the therapy based on a comparison between difference scores, or based on an initial predictive score. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In one embodiment a less aggressive therapy comprises no change in the therapy regimen. In one embodiment a less aggressive therapy comprises delaying treatment. In one embodiment a less aggressive therapy comprises selecting and administering less potent drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based therapies, non-drug-based therapies, or a combination of classes of drug-based therapies.

Therapies for CVD can include, without limitation, anticoagulants, antiplatelet agents, thrombolytic agents, antithrombotics, antiarrhythmic agents, agents that prolong repolarization, antihypertensive agents, vasodilator, antihypertensives, diuretics, inotropic agents, antianginal agents and the like. Non-limiting examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin. Non-limiting examples of antiplatelet agents include aspirin, a dextran, dipyridamole (persantin), heparin, sulfinpyranone (anturane), clopidrogel and ticlopidine (ticlid). Non limiting examples of thrombolytic agents include tissue plaminogen activator (activase), plasmin, pro-urokinase, urokinase (abbokinase) streptokinase (streptase), anistreplase/APSAC (eminase). Treatments for infections are well known in the art, and can generally be classified, without limitation, as antibiotics, antivirals, antifungals, homeopathic remedies, or anti-parasitics.

To identify additional therapeutics or drugs that are appropriate for a specific subject, a test sample from the subject can also be exposed to a therapeutic agent or a drug, and the level of one or more biomarkers can be determined. The level of one or more biomarkers can be compared to sample derived from the subject before and after treatment or exposure to a therapeutic agent or a drug, or can be compared to samples derived from one or more subjects who have shown improvements in inflammatory disease state or activity (e.g., clinical parameters or traditional laboratory risk factors) as a result of such treatment or exposure.

Clinical Assessments of the Present Teachings

In some embodiments of the present teachings, MBDA scores are tailored to the population, endpoints or clinical assessment, and/or use that is intended. For example, a MBDA score can be used to assess subjects for primary prevention and diagnosis, and for secondary prevention and management. For the primary assessment, the MBDA score can be used for prediction and risk stratification for future conditions or disease sequelae, for the diagnosis of inflammatory disease and CVD risk, for the prognosis of disease activity and rate of change, and for indications for future diagnosis and therapeutic regimens. For secondary prevention and clinical management, the MBDA score can be used for prognosis and risk stratification. The MBDA score can be used for clinical decision support, such as determining whether to defer intervention or treatment, to recommend preventive check-ups for at-risk patients, to recommend increased visit frequency, to recommend increased testing, and to recommend intervention. The MBDA score can also be useful for therapeutic selection, determining response to treatment, adjustment and dosing of treatment, monitoring ongoing therapeutic efficiency, monitoring therapy withdrawal, and indication for change in therapeutic regimen.

In some embodiments of the present teachings, the MBDA score can be used to aid in the diagnosis of inflammatory disease and predict CVD risk, and in the determination of the severity of inflammatory disease. The MBDA score can also be used for determining the future status of intervention such as, for example in RA, determining the prognosis of future joint erosion with or without treatment or CVD risk with or without treatment. Certain embodiments of the present teachings can be tailored to a specific treatment or a combination of treatments.

Clinical variables that can be used to adjust the MBDA score can include, for example, gender/sex, smoking status, age, race/ethnicity, disease duration, diastolic and systolic blood pressure, resting heart rate, height, weight, adiposity, body-mass index, serum leptin, family history, CCP status (i.e., whether subject is positive or negative for anti-CCP antibody), CCP titer, RF status, RF titer, ESR, CRP titer, menopausal status, and whether a smoker/non-smoker.

Systems for Implementing Risk Assessment Tests

Tests for measuring risk according to various embodiments of the present teachings can be implemented on a variety of systems typically used for obtaining test results, such as results from immunological or nucleic acid detection assays. Such systems may comprise modules that automate sample preparation, that automate testing such as measuring biomarker levels, that facilitate testing of multiple samples, and/or are programmed to assay the same test or different tests on each sample. In some embodiments, the testing system comprises one or more of a sample preparation module, a clinical chemistry module, and an immunoassay module on one platform. Testing systems are typically designed such that they also comprise modules to collect, store, and track results, such as by connecting to and utilizing a database residing on hardware. Examples of these modules include physical and electronic data storage devices as are well-known in the art, such as a hard drive, flash memory, and magnetic tape. Test systems also generally comprise a module for reporting and/or visualizing results. Some examples of reporting modules include a visible display or graphical user interface, links to a database, a printer, etc. See section Machine-readable storage medium, below.

One embodiment of the present invention can comprise a system for determining infection or CVD risk of a subject. In some embodiments, the system employs a module for applying a formula to an input comprising the measured levels of biomarkers in a panel, as described herein, and outputting a score. In some embodiments, the measured biomarker levels are test results, which serve as inputs to a computer that is programmed to apply the formula. The system may comprise other inputs in addition to or in combination with biomarker results in order to derive an output score; e.g., one or more clinical parameters such as therapeutic regimen, TJC, SJC, morning stiffness, arthritis of three or more joint areas, arthritis of hand joints, symmetric arthritis, rheumatoid nodules, radiographic changes and other imaging, gender/sex, age, race/ethnicity, disease duration, height, weight, body-mass index, family history, CCP status, RF status, ESR, smoker/non-smoker, etc. In some embodiments the system can apply a formula to biomarker level inputs, and then output a risk score that can then be analyzed in conjunction with other inputs such as other clinical parameters. In other embodiments, the system is designed to apply a formula to the biomarker and non-biomarker inputs (such as clinical parameters) together, and then report a composite output risk index.

A number of testing systems are presently available that could be used to implement various embodiments of the present teachings. See, for example, the ARCHITECT series of integrated immunochemistry systems—high-throughput, automated, clinical chemistry analyzers (ARCHITECT is a registered trademark of Abbott Laboratories, Abbott Park, Ill. 60064). See C. Wilson et al., "Clinical Chemistry Analyzer Sub-System Level Performance," American Association for Clinical Chemistry Annual Meeting, Chicago, Ill., Jul. 23-27, 2006; and, H J Kisner, "Product development: the making of the Abbott ARCHITECT," Clin. Lab. Manage. Rev. 1997 Nov.-Dec., 11(6):419-21; A. Ognibene et al., "A new modular chemiluminescence immunoassay analyzer evaluated," Clin. Chem. Lab. Med. 2000 March, 38(3):251-60; J W Park et al., "Three-year experience in using total laboratory automation system," Southeast Asian J. Trop. Med. Public Health 2002, 33 Suppl 2:68-73; D. Pauli et al., "The Abbott Architect c8000: analytical performance and productivity characteristics of a new analyzer applied to general chemistry testing," Clin. Lab. 2005, 51(1-2):31-41.

Another testing system useful for embodiments of the present teachings is the VITROS system (VITROS is a registered trademark of Johnson & Johnson Corp., New Brunswick, NJ)—an apparatus for chemistry analysis that is used to generate test results from blood and other body fluids for laboratories and clinics. Another testing system is the DIMENSION system (DIMENSION is a registered trademark of Dade Behring Inc., Deerfield Ill.)—a system for the analysis of body fluids, comprising computer software and hardware for operating the analyzers, and analyzing the data generated by the analyzers.

The testing required for various embodiments of the present teachings, e.g. measuring biomarker levels, can be performed by laboratories such as those certified under the Clinical Laboratory Improvement Amendments (42 U.S.C. Section 263(a)), or by laboratories certified under any other federal or state law, or the law of any other country, state or province that governs the operation of laboratories that analyze samples for clinical purposes. Such laboratories include, for example, Laboratory Corporation of America, 358 South Main Street, Burlington, NC 27215 (corporate headquarters); Quest Diagnostics, 3 Giralda Farms, Madison, NJ 07940 (corporate headquarters); and other reference and clinical chemistry laboratories.

Kits

Other embodiments of the present teachings comprise biomarker detection reagents packaged together in the form of a kit for conducting any of the assays of the present teachings. In certain embodiments, the kits comprise oligonucleotides that specifically identify one or more biomarker nucleic acids based on homology and/or complementarity with biomarker nucleic acids. The oligonucleotide sequences may correspond to fragments of the biomarker nucleic acids. For example, the oligonucleotides can be more than 200, 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a MBDA score, can be included in the kit; e.g., written, tape, VCR, or CD-ROM. The assay can for example be in the form of a Northern hybridization or a sandwich ELISA as known in the art.

In some embodiments of the present teachings, biomarker detection reagents can be immobilized on a solid matrix, such as a porous strip, to form at least one biomarker detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of biomarker present in the sample. The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. The nucleic acids on the array specifically identify one or more nucleic acid sequences represented by the MBDA markers. In various embodiments, the expression of one or more of the sequences represented by the MBDA markers can be identified by virtue of binding to the array. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, TX), Cyvera (Illumina, San Diego, CA), RayBio Antibody Arrays (RayBiotech, Inc., Norcross, GA), CellCard (Vitra Bioscience, Mountain View, CA) and Quantum Dots' Mosaic (Invitrogen, Carlsbad, CA).

Machine-Readable Storage Medium

A machine-readable storage medium can comprise, for example, a data storage material that is encoded with machine-readable data or data arrays. The data and machine-readable storage medium are capable of being used for a variety of purposes, when using a machine programmed with instructions for using said data. Such purposes include, without limitation, storing, accessing and manipulating information relating to the risk of a subject or population over time, or risk in response to treatment, or for drug discovery for inflammatory disease, etc. Data comprising measurements of the biomarkers of the present teachings, and/or the evaluation of infection or CVD risk from these biomarkers, can be implemented in computer programs that are executing on programmable computers, which comprise a processor, a data storage system, one or more input devices, one or more output devices, etc. Program code can be applied to the input data to perform the functions described herein, and to generate output information. This output information can then be applied to one or more output devices, according to methods well-known in the art. The computer can be, for example, a personal computer, a microcomputer, or a workstation of conventional design.

The computer programs can be implemented in a high-level procedural or object-oriented programming language, to communicate with a computer system such as for example, the computer system illustrated in FIG. 2. The programs can also be implemented in machine or assembly language. The programming language can also be a compiled or interpreted language. Each computer program can be stored on storage media or a device such as ROM, magnetic diskette, etc., and can be readable by a programmable computer for configuring and operating the computer when the storage media or device is read by the computer to perform the described procedures. Any health-related data management systems of the present teachings can be considered to be implemented as a computer-readable storage medium, configured with a computer program, where the storage medium causes a computer to operate in a specific manner to perform various functions, as described herein.

The biomarkers disclosed herein can be used to generate a "subject biomarker profile" taken from subjects who have inflammatory disease. The subject biomarker profiles can then be compared to a reference biomarker profile, in order to diagnose or identify subjects with increased infection or CVD risk. The biomarker profiles, reference and subject, of embodiments of the present teachings can be contained in a machine-readable medium, such as analog tapes like those readable by a CD-ROM or USB flash media, among others. Such machine-readable media can also contain additional test results, such as measurements of clinical parameters and clinical assessments. The machine-readable media can also comprise subject information; e.g., the subject's medical or family history. The machine-readable media can also contain information relating to other disease activity algorithms and computed scores or indices, such as those described herein.

EXAMPLES

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, *Proteins: Structures and Molecular Properties*, 1993, W. Freeman and Co.; A. Lehninger, Biochemistry, Worth Publishers, Inc. (current addition); J. Sambrook et al., *Molecular Cloning: A Laboratory Manual*, 2nd Edition, 1989; *Methods In Enzymology*, S. Colowick and N. Kaplan, eds., Academic Press, Inc.; *Remington's Pharmaceutical Sciences*, 18th Edition, 1990, Mack Publishing Company, Easton, PA; Carey and Sundberg, *Advanced Organic Chemistry*, Vols. A and B, 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, *Statistical Analysis with Missing Data,* 2nd Edition 2002, John Wiley and Sons, Inc., NJ; M. Pepe, *The Statistical Evaluation of Medical Tests for Classification and Prediction* (*Oxford Statistical Science Series*) 2003, Oxford University Press, Oxford, UK; X. Zhoue et al., *Statistical Methods in Diagnostic Medicine* 2002, John Wiley and Sons, Inc., NJ; T. Hastie et. al, *The Elements of Statistical Learning: Data Mining, Inference, and Prediction,* Second Edition 2009, Springer, NY; W. Cooley and P. Lohnes, *Multivariate procedures for the behavioral science* 1962, John Wiley and Sons, Inc. NY; E. Jackson, *A User's Guide to Principal Components* 2003, John Wiley and Sons, Inc., NY.

Example 1: Deriving a MBDA Risk Score for Infection and Cardiovascular Disease

This example demonstrates a method of determining myocardial infarction and serious infection risk in patients with rheumatoid arthritis (RA).

BACKGROUND

The goal of treatment for patients with RA is remission or low disease activity, and it's believed that a reduced systemic inflammatory burden may have non-articular benefits. Population-based research in RA studying hard endpoints including hospitalized infection and myocardial infarction (MI) is challenging because the relatively low prevalence of RA and outcome event rates limits statistical power. Administrative data from health plans and payers have high validity for studying large cohorts of patients with RA. While these data sources often lack clinical assessments of RA, results of lab tests that measure RA disease activity may provide objective measurements that can augment claims data.

One such measure is the multibiomarker disease activity (MBDA) test, The MBDA score is a validated tool that quantifies 12 serum protein biomarkers to assess disease activity in adult patients with rheumatoid arthritis (RA) (Curtis J R, et al., *Arthritis Care Res.* 64:1794-803 (2012)). The 12 MBDA serum protein biomarkers are VCAM-1, EGF, VEGF-A, IL-6, TNFRI, MMP-1, MMP-3, YKL-40, leptin, resistin, SAA, and CRP. Derivation of these 12 biomarkers is described fully in U.S. Pat. No. 9,200,324, which is hereby fully incorporated by reference in its entirety.

Serious infection events (SIE) and myocardial infarctions (MI) are among the most concerning adverse events (AE) that occur in rheumatoid arthritis (RA) patients. Given interest in quantifying the relationship between RA disease activity and serious adverse events (SAEs) and other health-related outcomes, we assembled a large cohort of patients with RA and Medicare coverage, and linked each patient to their MBDA lab test results. The MBDA score served as the measure of RA disease activity. Using this approach, we examined the association between the MBDA score and several outcomes including hospitalized infection, MI, and CHD events.

Methods

MBDA scores were linked to Medicare claims (2011-2014) at a patient-level for individuals with RA who had greater than 12 months of Medicare coverage. Patients with other autoimmune diseases were excluded. Results of the MBDA tests for all Medicare beneficiaries were obtained directly from the laboratory provider (Crescendo Biosciences, South San Francisco, California, USA) for this analysis. The data provided included the MBDA score, leptin and CRP values, along with patients' birth date, sex, state of residence, blood sample collection date, referral physician's national provider identification (NPI) number and dates of service. A linkage between MBDA test and Medicare claims (billed as Healthcare Common Procedure Coding System (HCPCS) codes 84999, 84179 and 84190) was considered successful if a unique match was made between the CMS data and the laboratory's database on these factors: (1) full birth date, (2) sex, (3) NPI number and (4) date of service. The study was governed by a Data Use Agreement from the CMS.

To be included in the study, a patient must have had (1) at least one MBDA score linked to Medicare claims that was considered valid (see definition below), and (2) at least 365 continuous days of Medicare with part D (pharmacy) coverage before the first valid MBDA test date. The later of these two dates was defined as the start of follow-up ('index date'). This 365-day baseline period was used to assess comorbidities and other baseline characteristics. Patients were excluded if (1) there was an International Classification of Diseases (ICD)-9 diagnosis code for ankylosing spondylitis, inflammatory bowel disease psoriasis, psoriatic arthritis, systemic lupus erythematosus, malignancy (ignoring non-melanoma skin cancer), polymyalgia rheumatic and giant cell arteritis in the 12-month baseline period; and (2) they had initiated any non-tumour necrosis factor (TNF) biologic or synthetic targeted DMARDs including abatacept, anakinra, rituximab, tocilizumab, ustekinumab or apremilast or tofacitinib in the 183 days before the index date. This latter restriction was applied given the possibility that some biologics might have a differential influence on the biomarker profile. For the MI and CHD outcomes, patients with prior MI (ICD-9 diagnosis code 410.xx or 412.xx) or any HCPCS code for coronary artery bypass grafting (CABG) or percutaneous coronary intervention (PCI) during the baseline period were also excluded.

MBDA scores were not considered valid for this analysis and were therefore excluded (n=10,996) if patients had an outpatient infection (based on receipt of outpatient antibiotics), vaccination (pneumococcal, influenza or herpes zoster, based on HCPCS codes) or hospitalization (based on any inpatient claim from Medicare) within the 21 days prior to the index date, given the possibility that these events might affect the MBDA score. All MBDA tests were ordered as part of rheumatologists' standard of care for their patients with RA. Most patients (72.9%) had only one MBDA test result available for the current analysis, while 18.2% had two MBDA tests, and 8.9% had three or more test results.

The five outcomes of interest included (1) hospitalized serious infectious event for pneumonia or sepsis with a discharge diagnosis code in the primary position, generally indicating the main reason for hospitalization (SIE-primary); (2) hospitalized infection for pneumonia or sepsis (primary or non-primary position discharge diagnosis code, SIE-all); (3) hospitalized MI (primary or non-primary position discharge diagnosis code); (4) CHD events including MI and PCI and CABG procedures; and (5) total costs and medical costs as paid for by the Medicare programme. The algorithms to identify the hospitalized infections and MI events as defined above have been previously shown to have high validity, with positive predictive values in the 85%-95% range.

Baseline characteristics of the RA cohort were assessed at the time of the first MBDA test, stratified by MBDA category (low, moderate and high disease activity). Event rates and 95% CIs were computed for each of the four outcomes.

Cox proportional hazards models with MBDA score as a time-dependent variable were used to evaluate the association between the MBDA score and the first occurrence of each outcome of interest, controlling for potential confounders that were selected based on their hypothesized associations with the MBDA score and the outcomes under study. These covariates were measured at baseline, and included age, sex and race, and baseline history of heart failure, stroke, abdominal aortic aneurysm, peripheral arterial disease, atrial fibrillation, diabetes, hyperlipidaemia, hypertension, obesity, smoking, chronic kidney disease, chronic obstructive pulmonary disease, pneumonia, sepsis, fibromyalgia, peptic ulcer disease, fracture and skin ulcer, all ascertained using diagnosis codes from physician office visits or hospitalizations. Covariates also included health-seeking behaviors, including cancer screening including prostate-specific antigen, Papanicolaou smear and mammography. RA factors were controlled for baseline hydroxychloroquine, leflunomide, sulfasalazine, biologic use, methotrexate (MTX) dose in the preceding 4 months, and glucocorticoid dose in the preceding 6 months, measured by summing the cumulative prednisone-equivalent dose dispensed over this period, dividing by 183 days, and categorized as none, ≤7.5 mg/day and >7.5 mg/day. A sensitivity analysis censored follow-up at 12 months after each MBDA test so as to avoid misclassification of the score over time.

After examining the correlation between the MBDA score and CRP and a recalculated biomarker score without CRP, the analyses were repeated using the MBDA score without CRP as the main independent variable. Additionally, as obesity has been associated with CHD events in some studies, sensitivity analyses that also adjusted for leptin was also conducted, which has been shown to be a proxy for obesity and fat mass. Leptin was log-transformed to be more linearly related to outcomes. The proportional hazard assumption was tested using the method described by Lin et al (*Biometrika* 80:557-72, 1993) and no violations were present. All analyses were conducted on SAS V.9.4.

Results

A total of 17,433 patients were eligible for the SIE analysis, and 16,796 for the MI/CHD analysis. Baseline characteristics (Table 1) of patients in the high MBDA category were mean (SD) age 69 (10) years, 79% women, 80% white, and 37% disabled. RA therapies included biologics (16%), MTX (55%), other non-biologic DMARDs (41%), and oral glucocorticoids (60%).

Characteristics of patients in lower MBDA categories suggested that compared to patients with higher MBDA scores, patients were somewhat younger and had a slightly lower burden of comorbidities, with less glucocorticoid use and more biologic use (Table 1).

TABLE 1

| MBDA Score (low, moderate, high) | Overall N = 17,433 | <30 n = 2,393 | 30-44 n = 6,887 | >44 n = 8,153 |
|---|---|---|---|---|
| Age in years, Mean (SD) | 68.9 (10.7) | 66.3 (11.4) | 69.2 (10.3) | 69.5 (10.6) |
| Score*, Mean (SD) | 44.1 (14.0) | 21.9 (5.3) | 37.9 (4.1) | 55.8 (9.2) |
| Race, % | | | | |
| Black | 9.7 | 7.7 | 8.9 | 11.0 |
| White | 80.7 | 79.4 | 81.4 | 80.4 |
| Other | 9.6 | 13.0 | 9.7 | 8.6 |
| Co-morbidities, % | | | | |
| Acute myocardial infarction** | 1.1 | 0.5 | 1.0 | 1.3 |
| Coronary heart disease | 20.3 | 16.1 | 19.6 | 22.0 |
| Heart failure | 7.1 | 3.0 | 5.3 | 9.8 |
| Stroke | 6.0 | 4.7 | 5.6 | 6.6 |
| Abdominal aortic aneurism | 1.1 | 0.8 | 1.1 | 1.1 |
| Peripheral arterial disease | 3.4 | 2.3 | 3.2 | 3.9 |
| Atrial fibrillation | 7.9 | 4.6 | 6.8 | 9.8 |
| Diabetes | 25.0 | 17.8 | 22.6 | 29.2 |
| Hyperlipidemia | 55.4 | 51.5 | 57.0 | 55.2 |
| Hypertension | 67.2 | 56.0 | 65.2 | 72.1 |
| Obesity | 7.2 | 4.4 | 6.6 | 8.6 |
| Smoking | 12.2 | 9.5 | 11.0 | 14.1 |
| Chronic kidney disease | 11.6 | 6.1 | 9.7 | 14.8 |
| Chronic obstructive pulmonary disease | 25.4 | 19.3 | 23.0 | 29.2 |
| Pneumonia | 5.3 | 2.6 | 4.1 | 7.0 |
| Sepsis | 1.8 | 0.5 | 1.4 | 2.5 |
| Medication use, % | | | | |
| Biologic DMARDs, % | 37.0 | 21.2 | 17.5 | 15.5 |
| HC, LEF or SSZ, % | 40.2 | 38.9 | 39.2 | 41.4 |
| Methotrexate, mg/week | | | | |
| No use | 45.7 | 49.4 | 45.9 | 44.5 |
| ≤10 | 47.9 | 43.5 | 47.6 | 49.4 |
| >10, ≤15 | 5.1 | 5.6 | 5.2 | 4.8 |
| >15, ≤20 | 1.1 | 1.4 | 1.1 | 1.2 |
| >20 | 0.2 | 0.2 | 0.3 | 0.1 |
| Prednisone equivalent steroid dose, mg/d | | | | |
| No use | 46.7 | 57.5 | 51.2 | 39.7 |
| 0< to ≤7.5 | 33.2 | 30.1 | 33.7 | 33.7 |
| >7.5 | 20.1 | 12.4 | 15.1 | 26.7 |

TABLE 1-continued

| MBDA Score (low, moderate, high) | Overall N = 17,433 | <30 n = 2,393 | 30-44 n = 6,887 | >44 n = 8,153 |
|---|---|---|---|---|
| Health behavior, % | | | | |
| Prostate-specific antigen*** | 48.2 | 53.7 | 50.3 | 44.2 |
| Papanicolaou smear**** | 12.3 | 17.2 | 13.1 | 10.4 |
| Mammography**** | 43.6 | 48.3 | 47.5 | 39.1 |
| Qualified for Medicare for reason other than age (e.g., disability) | 37.8 | 38.9 | 35.9 | 39.1 |

*First score
**these patients included in infection analysis but excluded from MI and CVD analysis
****men only
****women only
HCQ = hydroxychloroquine; LEF = leflunomide; SSZ = sulfasalazine In 16,424 person-years of follow-up, there were 452 SIE-primary events (Table 2), 653 SIE-secondary events (Table 3), 653 SIE-primary or secondary events (Table 4), 132 MI events (Table 5), and 181 CHD events (Table 6). Higher MBDA scores, modelled in quartiles were associated with increasing outcome rates, as were MBDA scores modelled per 10 unit increase or using established RA disease activity cutpoints. After multivariable adjustment, higher MBDA scores were associated with statistically significantly higher rates of SIE-primary and SIE-all events and higher MI and CHD rates. The sensitivity analysis that censored follow-up 12 months after each MBDA score yielded similar results.

TABLE 2

| | SIE-primary n = 452 events | | |
|---|---|---|---|
| MBDA | IR | aHR (95% CI) | |
| All scores Categorical score | 2.75 (2.51 to 3.02) | 1.32 (1.24 to 1.41) | |
| Low (<30) | 0.74 (0.46 to 1.17) | Referent | |
| Moderate (30-44) | 1.98 (1.68 o 2.35) | 2.18 (1.33 to 3.59) | |
| High (>44) | 4.17 (3.72 to 4.67) | 3.56 (2.18 to 5.81) | |
| Quartiles | | | |
| Q1 (<35) | 1.07 | Referent | |
| Q2 (35-42) | 2.06 | 1.87 (1.30, 2.67) | |
| Q3 (43-52) | 3.09 | 2.78 (1.96, 3.95) | |
| Q4 (53-100) | 4.94 | 4.45 (3.21, 6.19) | |

SIE = serious infection event; IR = incidence rate per 100 patient years; aHR = adjusted hazard ratio, controlling for age, sex, and race.

TABLE 3

| | SIE-secondary n = 653 events | |
|---|---|---|
| MBDA | IR | aHR (95% CI) |
| All scores Categorical score | 4.00 | 1.48 (1.41, 1.55) |
| Low (<30) | 1.19 | Referent |
| Moderate (30-44) | 2.73 | 2.18 (1.47, 3.23) |
| High (>44) | 6.17 | 4.91 (3.36, 7.18) |
| Quartiles | | |
| Q1 (<35) | 1.58 | Referent |
| Q2 (35-42) | 2.79 | 1.71 (1.27, 2.38) |
| Q3 (43-52) | 4.62 | 2.81 (2.11, 3.75) |
| Q4 (53-100) | 7.28 | 4.44 (3.89, 5.82) |

SIE = serious infection event; IR = incidence rate per 100 patient years; aHR = adjusted hazard ratio, controlling for age, sex, and race.

TABLE 4

| | SIE-primary or secondary n = 653 events | |
|---|---|---|
| MBDA | IR | aHR (95% CI) |
| All scores Categorical score | 4.00 (3.71 to 4.32) | 1.34 (1.27 to 1.41) |
| Low (<30) | 1.19 (0.83 to 1.72) | Referent |
| Moderate (30-44) | 2.73 (2.36 to 3.15) | 1.85 (1.25 to 2.76) |
| High (>44) | 6.17 (5.62 to 6.78) | 3.34 (2.26 to 4.91) |

SIE = serious infection event; IR = incidence rate per 100 patient years; aHR = adjusted hazard ratio, controlling for age, sex, and race.

TABLE 5

| | MI-primary or secondary n = 132 events | |
|---|---|---|
| MBDA | IR | aHR |
| All scores Categorical score | 0.82 (0.69 to 0.97) | 1.09 (0.97 to 1.23) |
| Low (<30) | 0.42 (0.22 to 0.78) | Referent |
| Moderate (30-44) | 0.80 (0.61 to 1.04) | 1.53 (0.77 to 3.07) |
| High (>44) | 0.98 (0.78 to 1.24) | 1.52 (0.77 to 3.01) |
| Quartiles | | |
| Q1 (<35) | 0.47 | Referent |
| Q2 (35-42) | 0.83 | 1.56 (0.97, 2.52) |
| Q3 (43-52) | 0.92 | 1.93 (1.32, 3.06) |
| Q4 (53-100) | 1.09 | 2.02 (1.27, 3.21) |

MI = myocardial infarction; IR = incidence rate per 100 patient years; aHR = adjusted hazard ratio, controlling for age, sex, and race.

TABLE 6

| | CHD-primary or secondary n = 181 events | |
|---|---|---|
| MBDA | IR | aHR |
| All scores Categorical score | 1.13 (0.98 to 1.31) | 1.09 (0.98 to 1.22) |
| Low (<30) | 0.67 (0.41 to 1.09) | Referent |
| Moderate (30-44) | 1.05 (0.83 to 1.33) | 1.34 (0.77 to 2.34) |
| High (>44) | 1.36 (1.11 to 1.66) | 1.42 (0.82 to 2.47) |
| Quartiles | | |
| Q1 (<35) | 0.67 | Referent |
| Q2 (35-42) | 1.08 | 1.56 (0.97, 2.52) |

TABLE 6-continued

| | CHD-primary or secondary n = 181 events | |
|---|---|---|
| MBDA | IR | aHR |
| Q3 (43-52) | 1.34 | 1.93 (1.32, 3.06) |
| Q4 (53-100) | 1.42 | 2.02 (1.27, 3.21) |

CHD = MI, PCI, or CABG; IR = incidence rate per 100 patient years; aHR = adjusted hazard ratio, controlling for age, sex, and race.

The crude rates of all outcomes were associated with increasing MBDA score in a dose-response fashion (Tables 2-6), using either established cut-points or quartiles. After adjustment for age, sex, and race, higher MBDA scores were associated with all outcomes of interest.

There was a high correlation between the MBDA score and the MBDA score without CRP (r=0.97). Higher MBDA scores without CRP were associated with increased outcome rates. For the MI and CHD outcomes, there was a dose-response relationship between higher quartiles of the MBDA without CRP and the SIE outcomes, but for MI and CHD events quartiles 2-4 were associated with similar risk. In analyses, with and without exclusion of CRP or adjustment for leptin, the adjusted HR for MI and CHD events in the highest three compared with the lowest quartile of disease activity was between 1.5 and 1.8 (Table 7). Table 7 provides the adjusted hazard ratios controlling for age, sex and race, heart failure, stroke, abdominal aortic aneurysm, peripheral arterial disease, atrial fibrillation, diabetes, hyperlipidaemia, hypertension, obesity, smoking, chronic kidney disease, chronic obstructive pulmonary disease, pneumonia, sepsis, fibromyalgia, peptic ulcer disease, fracture, skin ulcer, prostate-specific antigen, Papanicolaou smear, mammography, use of hydoxychloroquine, leflunomide, sulfasalazine or biologics, glucocorticoid dose, methotrexate dose, and reason for eligibility for Medicare (e.g., disability).

Recognizing that leptin is part of the MBDA score, leptin as a model covariate was associated with a protective effect for both MI (adjusted HR for log-transformed leptin=0.79, 95% CI 0.69 to 0.91) and CHD (adjusted HR=0.83, 95% CI 0.73 to 0.94). There was no statistically significant interaction between sex and log-transformed leptin (P=0.16 for both AMI and CHD events).

risk-stratify patients for these serious adverse events will help clinicians identify those patients at highest risk.

Example 2: Prediction of CVD in RA Patients Using a Multi-Biomarker Disease Activity (MBDA) Test Coupled with Clinical Factors This example demonstrates a method of predicting CVD risk using a multi-biomarker disease activity (MBDA) test coupled with clinical factors in patients with rheumatoid arthritis (RA).

INTRODUCTION

RA patients are at higher risk for CVD events, yet the role of systemic inflammation and the influence of traditional CVD risk factors is unclear with respect to risk prediction in RA.

Methods

A U.S. cohort of RA patients with multi-biomarker disease activity (MBDA) test results linked to Medicare claims data was derived. Patients had >=1 year baseline with Medicare coverage prior to their first MBDA test. Exclusions were past MI, PCI/CABG, stroke, or cancer. Follow-up ended at the earliest of 1) CVD event; 2) other than CVD cause of death; 3) loss of coverage; or 4) Dec. 31, 2014. The composite CVD event comprised of incident MI, stroke or fatal CVD event, using validated algorithms. MBDA scores were grouped as low (<30), moderate (30-44), and high (>44). Other predictors included demographics, healthcare utilization, and comorbidities. Three separate models were developed using Cox regression. Model 1 included age, sex and race. Model 2 included age, sex race, 9 comorbidities and CVD medication classes, plus interaction terms. Model 3 included age, sex, and race plus categorized MBDA score. The net reclassification index (NRI) was then calculated for model 2 and 3 compared to model 1. The observed vs. predicted probability of CVD event was then calculated for each model, with risk categorized as low (<7.5), moderate (7.5-<15) and high (>=15) per 1000 person-years.

Results

A total of 15,757 RA patients were included; mean (SD) age 68.6(10.8) years, 80% female, 80% white. A total 209

TABLE 7

| | aHR (95% CI) | aHR (95% CI) adjusted for leptin | aHR (95% CI) excluding CRP | aHR (95% CI) excluding CRP, adjusted for leptin |
|---|---|---|---|---|
| MI events | | | | |
| Quartile 1 | Referent | Referent | Referent | Referent |
| Quartiles 2-4 | 1.52 (0.92 to 2.50) | 1.65 (1.00 to 2.72) | 1.70 (1.01 to 2.87) | 1.86 (1.10 to 3.15) |
| CHD events | | | | |
| Quartile 1 | Referent | Referent | Referent | Referent |
| Quartiles 2-4 | 1.54 (1.01 to 2.34) | 1.64 (1.08 to 2.51) | 1.53 (1.01 to 2.32) | 1.64 (1.07 to 2.50) | aHR, adjusted HR; CHD, coronary heart disease; IR, incidence rate per 100 patient years; MBDA, multibiomarker disease activity; MI, myocardial infarction, SIE, serious infection event.

Conclusion

In a RA population predominantly consisting of older individuals, higher MBDA scores were associated with increased risk for hospitalized infection, MI, and CHD events. The role of RA disease activity and associated systemic inflammation has not been well examined as it relates to these outcomes. Use of the MBDA score to CVD events occurred in 14,843 person years. The median (IQR) follow up time was 0.84 (0.41, 1.27) year. The maximum event time was at 2.7 year. While all models had reasonable discrimination and calibration (e.g., model 3 shown in FIG. 2), discrimination and calibration of model 3 was better than model 1 and model 2 (sum of absolute difference between observed and predicted probability was 0.56, 0.57 and 0.33 for model 1, model 2 and model 3, respectively). Compared to model 1, model 2 resulted in a positive overall NRI of 0.214 (non-event NRI=0.173, event NRI=0.041); model 3 result a positive overall NRI of 0.279 (non-event NRI=0.092, event NRI=0.187), consistent with more accurate CVD event classification.

Conclusion

This example shows that an algorithm consisting of age, sex and race plus a multi-biomarker score can provide an accurate method to predict short term CVD risk in RA.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

The invention claimed is:

1. A method for treating cardiovascular disease (CVD) or infection in a subject with rheumatoid arthritis (RA), the method comprising:
performing an immunoassay on a sample from the subject to generate a dataset comprising protein level data for at least four protein markers of the group comprising chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); and, vascular endothelial growth factor A (VEGFA), wherein the at least four protein markers comprise LEP, CRP, CHI3L1, and MMP1; and
calculating a risk score for the sample indicating CVD or infection present in the subject by combining the dataset with a clinical parameter and a clinical assessment; and
administering a therapeutic regimen to the subject comprising one or more of:
administering a therapeutic compound selected from a Disease-modifying antirheumatic drug (DMARD), a biologic DMARD, a non-steroidal anti-inflammatory drug (NSAID), and a corticosteroid;
administering dietary modification and/or supplementation; and
administering bariatric surgical intervention.

2. The method of claim 1, wherein the infection is associated with rheumatoid arthritis (RA).

3. The method of claim 1, wherein the infection is a serious infection event.

4. The method of claim 1, wherein the DMARD is selected from methotrexate (MTX), azathioprine (AZA), bucillamine (BUC), chloroquine (CQ), cyclosporine, doxycycline (DOXY), hydroxychloroquine (HCQ), intramuscular gold (IM gold), leflunomide (LEF), levofloxacin (LEV), sulfasalazine (SSZ), folinic acid, D-pencillamine, gold auranofin, gold aurothioglucose, gold thiomalate, cyclophosphamide, chlorambucil, infliximab, adalimumab, etanercept, golimumab, anakinra, abatacept, rituximab, and tocilizumab.

5. The method of claim 1, wherein the clinical parameter is a selected from age, sex, smoking status, adiposity, body mass index (BMI), and race/ethnicity.

6. The method of claim 5, wherein the clinical parameters are age, sex, and race/ethnicity.

7. The method of claim 1, further comprising a period of monitoring the subject's symptoms before administering treatment.

8. The method of claim 1, wherein the clinical assessment is selected from a Disease Activity Score (DAS), a DAS28, a DAS28-CRP, a DAS28-ESR, a Sharp score, a tender joint count (TJC), a swollen joint count (SJC), a Health assessment questionnaire (HAQ), a modified HAQ (mHAQ), a multi-dimensional HAQ (MD HAQ), a visual analog scale (VAS), a physician global assessment VAS, a patient global assessment VAS, a pain VAS, a fatigue VAS, an overall VAS, a sleep VAS, a simplified disease activity index (SDAI), a clinical disease activity index (CDAI), a routine assessment of patient index data (RAPID), a RAPID3, a RAPID4, a RAPID5, an American College of Rheumatology score (ACR), an ACR20, an ACR50, an ACR70, a SF-36, a RA MRI score (RAMRIS), a total Sharp score (TSS), a van der Heijde-modified TSS, a Sharp-van der Heijde score (SHS), a Larsen score, a CRP titer, and an erythrocyte sedimentation rate (ESR).

9. The method of claim 1, wherein the immunoassay comprises a multiplex assay.

10. The method of claim 1, wherein the immunoassay comprises:
obtaining the blood sample, wherein the blood sample comprises the protein markers;
contacting the blood sample with a plurality of distinct reagents;
generating a plurality of distinct complexes between the reagents and markers; and
detecting the complexes to generate the data.

11. The method of claim 1, wherein the calculating a risk score uses a reference group of at least 10,000 patients.

12. The method of claim 1, wherein the cardiovascular disease is a coronary heart disease (CHD).

13. The method of claim 12, wherein the CHD is one or more of myocardial infarction (MI), percutaneous coronary intervention (PCI), and coronary artery bypass grafting (CABG).

14. The method of claim 1, wherein the risk score is adjusted to a scale of 1-100.

15. The method of claim 14, wherein a threshold for indicating risk of CVD or infection is 30.

16. The method of claim 1, further comprising monitoring a response of the subject to a treatment by obtaining one or more additional risk scores for the subject after the treatment.

17. The method of claim 1, wherein the calculating a risk score uses a statistical tool to derive an interpretation function based on a predictive model of the subject's inflammatory disease.

18. The method of claim 17, wherein the statistical tool comprises one or more of Cox proportional hazards, clustering algorithms, analysis of variants (ANOVA), Adaboosting, Classification and Regression Trees (CART), boosted CART, Random Forest (RF), Recursive Partitioning Trees (RPART), Curds and Whey (CW), Curds and Whey-Lasso, principal component analysis (PCA), factor rotation analysis, Linear Discriminant Analysis (LDA), Eigengene Linear Discriminant Analysis (ELDA), quadratic discriminant analysis, Discriminant Function Analysis (DFA), Hidden Markov Models, kernel density estimation, kernel partial least squares algorithm, kernel matching pursuit algorithm, kernel Fisher's discriminate analysis algorithm, kernel principal components analysis algorithm; linear regression, Stepwise Regression, Forward-Backward Variable Stepwise Regression, Lasso shrinkage and selection, Elastic Net regularization and selection, Lasso and Elastic Net-regularized generalized linear model, Logistic Regression (LogReg), Kth-nearest neighbor (KNN), non-linear regression, classification, neural networks, partial least square, rules based classification, shrunken centroids (SC), sliced inverse regression, Standard for the Exchange of Product model data, Application Interpreted Constructs (StepAIC), super principal component (SPC) regression, Support Vector Machines (SVM), and Recursive Support Vector Machines (RSVM).

\* \* \* \* \*